United States Patent [19]

Swallow et al.

[11] Patent Number: 4,527,402
[45] Date of Patent: Jul. 9, 1985

[54] PROGRAM-CONTROLLED KNITTING MACHINE, METHOD AND PRODUCTS THEREOF

[75] Inventors: Roger T. Swallow, Asheboro; William R. Jackson, Raleigh; Jack D. Pierce, Asheboro, all of N.C.

[73] Assignee: Rampon Products, Inc., Asheboro, N.C.

[21] Appl. No.: 427,911

[22] Filed: Sep. 29, 1982

[51] Int. Cl.³ .......................... D04B 9/46; G06G 7/64; A41F 13/00; A41B 11/00

[52] U.S. Cl. ........................ 66/55; 66/132 R; 66/232; 364/470; 364/468; 364/469; 128/165; 2/239; 2/409

[58] Field of Search ............... 364/469, 470, 413, 468, 364/900; 66/219, 222, 232, 55, 132 R, 172 E, 178 A; 128/165; 2/239, 409

[56] References Cited

U.S. PATENT DOCUMENTS

| | | | |
|---|---|---|---|
| 2,807,946 | 10/1957 | Virchaux | 66/184 |
| 2,816,361 | 12/1957 | Jobst | 128/165 |
| 3,069,881 | 12/1962 | Warren | 66/154 |
| 3,232,079 | 2/1966 | Levine et al. | 66/154 |
| 3,670,527 | 6/1972 | Bourgeois | 66/232 |
| 3,861,178 | 1/1975 | Kouklik et al. | 66/155 |
| 3,866,442 | 2/1975 | Kouril et al. | 66/50 R |
| 3,890,016 | 6/1975 | Grozinger | 66/232 |
| 3,940,951 | 3/1976 | Christiansen | 66/222 X |
| 3,983,370 | 9/1976 | Caspi et al. | 364/470 |
| 4,018,064 | 4/1977 | Doslik | 66/232 |
| 4,019,036 | 4/1977 | Hiramatsu et al. | 364/470 |
| 4,048,818 | 9/1977 | Cueman | 66/172 E |
| 4,132,368 | 1/1979 | Scheiss et al. | 66/132 X |
| 4,240,160 | 12/1980 | Imboden et al. | 66/178 A X |

FOREIGN PATENT DOCUMENTS

| | | | |
|---|---|---|---|
| 0026425 | 8/1981 | European Pat. Off. | 66/55 |
| 2631858 | 2/1977 | Fed. Rep. of Germany | 66/55 |

Primary Examiner—Jerry Smith
Assistant Examiner—Jon D. Grossman
Attorney, Agent, or Firm—B. B. Olive

[57] ABSTRACT

A program-controlled knitting machine provides a method of knitting circular knit elasticized tubular goods, e.g., compressive stockings, in which the size of the goods and the amount of compression asserted when worn are controlled according to the specific size and needs of the individual using the goods.

22 Claims, 34 Drawing Figures

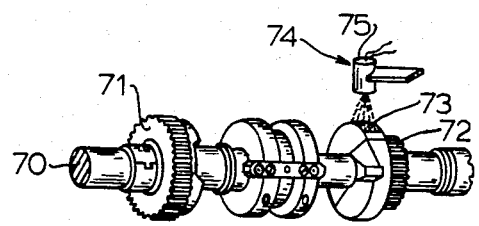
FIG. 15
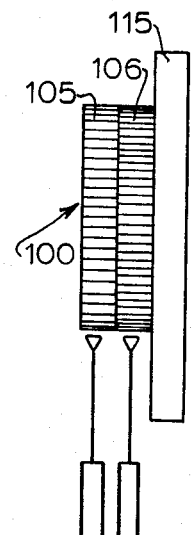
FIG. 18
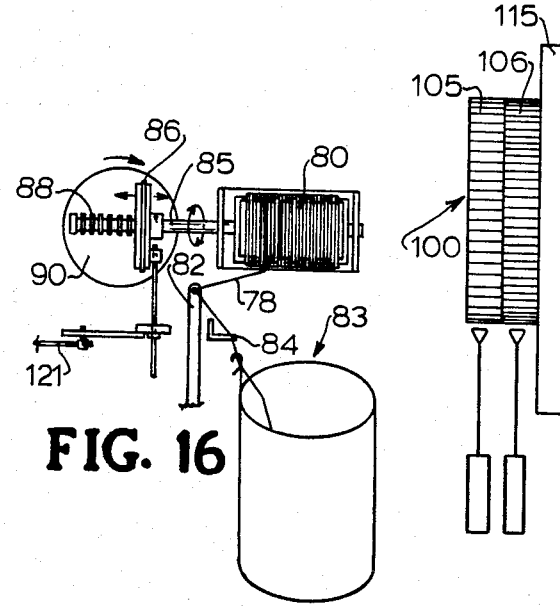
FIG. 16
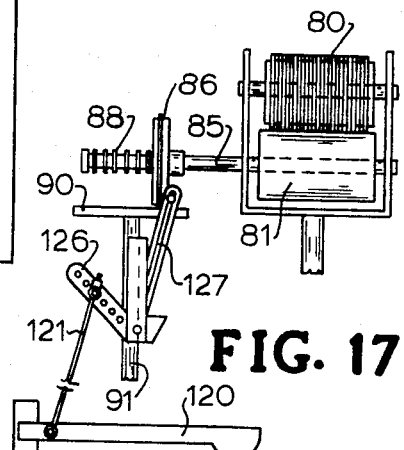
FIG. 17
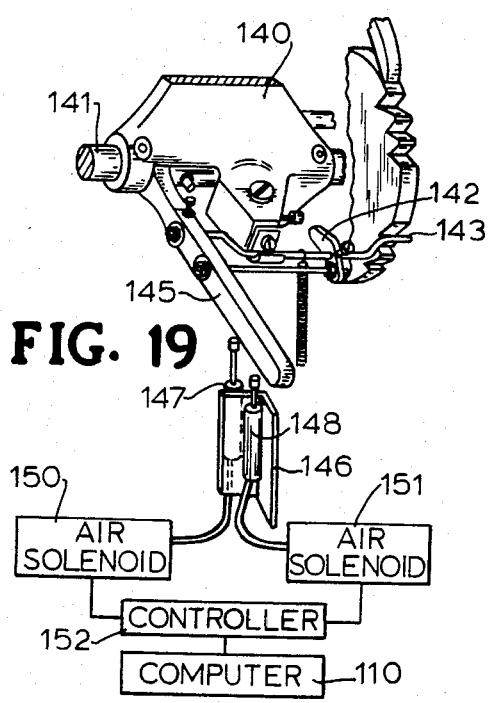
FIG. 19
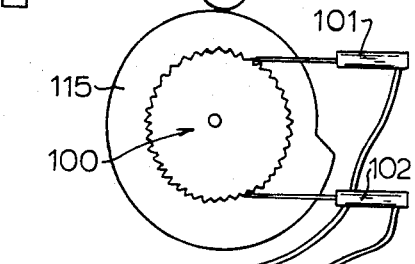
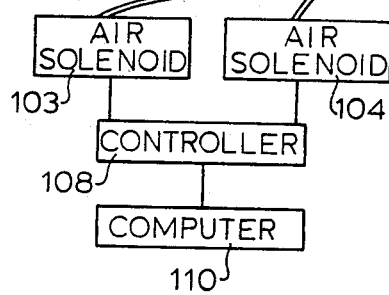

PROGRAM-CONTROLLED KNITTING MACHINE, METHOD AND PRODUCTS THEREOF

CROSS-REFERENCE TO RELATED COPENDING APPLICATIONS

This application relates to the subject matter of separately-filed copending applications Ser. No. 428,111, now U.S. Pat. No. 4,502,301, filed Sept. 29, 1982, entitled "Support Stocking Product or the Like" and now abandoned application Ser. No. 427,912, filed Sept. 29, 1982, entitled "Measuring Information Tape and Method For Support Stocking".

TECHNICAL FIELD

The invention relates to circular knitting machines and methods and to circular knit goods, particularly as they relate to the knitting of compressive stockings, and the like, for therapeutic use with a program-controlled knitting machine.

BACKGROUND ART

While the invention is regarded as having application to the knitting of goods other than compressive stockings, the provision of an improved knitting machine and method for knitting compressive stockings as well as an improved compressive stocking construction are used as illustrative examples of how the invention is applied. The background art is thus explained with these examples in mind.

It has long been known that elastic support stockings provide effective treatment for various chronic venous insufficiences. In some instances, the patient can be fitted with immediately-available, ready-made hosiery. However, because of the wide range of leg lengths and sizes, some patients require elastic support stockings made to a specific prescription for the patient's individual requirements.

One conventional method for making a compressive stocking according to a specific patient prescription involves measuring the patient's limb to be fitted at various locations along the length of the limb, cutting a piece of flat elastic fabric to conform to the patient's specific limb dimensions and then completing the stocking by joining the edges into a longitudinal seam. U.S. Pat. No. 2,816,361 describes such a method for cutting an elastic fabric blank corresponding to the dimensions of a specific patient recorded on a special tape device and then seaming the blank at the edges to provide a compressive stocking corresponding to a particular patient's specific needs. U.S. Pat. No. 2,807,946 describes a method of making a shaped compressive stocking on a circular knitting machine by increasing and decreasing the tension applied to the elastic or so-called "rubber" feed during knitting. While the specific type of machine control contemplated in U.S. Pat. No. 2,807,946 is not described, it would be expected that such rubber feed tension control would be under mechanical control on the machine.

In view of the fact that the present invention is directed in part to a program-controlled knitting operation it is also recognized that circular knitting machines have previously been operated under program control as distinct from use of a conventional pattern drum, or the like. For example, U.S. Pat. No. 3,069,881 teaches a punched card system with means to read the cards so as to control the knitting machine elements during the knitting sequence.

U.S. Pat. No. 3,232,079, in another example of a program-controlled circular knitting machine discloses a circular knitting machine in which program responsive electrical control means control various knitting elements, including raising and lowering the cylinder, to control the form of the circular knit fabric produced on the machine. However, this patent makes no suggestion or teaching for storing body, e.g., leg dimensions, or the like, for a specific patient and using this information in conjunction with known compressive characteristics obtainable from various machine settings also stored as a means for knitting a compressive stocking under program control to a specific prescription.

U.S. Pat. Nos. 3,670,527; 3,861,178; 3,866,442 and 4,018,064 further exemplify the state of the art with regard to program-controlled knitting machines.

Recognition is also given to the fact that storing of a specific size in memory and controlling a knitting machine to knit such size has been known. However, such machines do not provide for accommodation to a specific patient's needs nor do such machines progressively control both size and pressure.

With the above background art in mind, it becomes apparent that the art has not provided a satisfactory method for making compressive stockings according to prescription so as to provide a graduated pressure profile suited to the particular patient's limb dimensions and medical requirements. More specifically, none of the prior art methods or prior art circular knitting machines are adapted to produce a compressive stocking with a smooth, graduated transition in pressure from the ankle, through each leg segment point up to the gluteal furrow and with pressures determined so as to satisfy a physician-specified pressure profile based on the patient's needs. A critical analysis of so-called customized or prescription-made compressive support stockings according to the prior art reveals undesirable transitions in pressure. Also, the pressures do not correspond to the most desirable pressure profile and the profile is generally not precisely reproducible when a need for replacement occurs.

DISCLOSURE OF INVENTION

The circular knitting method and apparatus and circular knitted product of the invention are based in general on providing compressive stockings or other therapeutic-type, tubular knit goods in which the size and amount of compression obtained are knit under program control. Further, such size and amount of compression are fitted to the specific and graduated size of the patient's limb, the specific amount of compression and the specific pressure profile needed for the particular patient's medical condition.

Using compressive stockings as an example of the type of goods to which the invention is applied, the size and degree of graduated compression obtained are controlled by controlling selected machine elements under program control having access to a data bank in which information is stored relating some known predetermined number of combinations of machine settings to known and measured combinations of size and degree of compression. Using this prestored data, other data related to a patient's specific limb dimensions and a program for optimizing the selection of machine settings based on both sets of data, the desired stocking is knit and the desired graduated size and degree of compression are obtained by controlling the selected machine elements under program control.

In the illustrative embodiment, the cylinder height and feed speed for the elastic thread, i.e., the so-called "rubber" feed, are the controlled machine elements. The first-mentioned set of data is obtained by knitting, insofar as is practicable, a set of sample tubes based on a selected number of possible cylinder height positions and a selected number of possible rubber feed positions. Not all of the possible machine setting combinations are knit since some of the possible cylinder height-rubber feed combinations are impractical to knit. However, a sufficiently large number of samples are knit to provide a suitable data base from which optimal machine settings can be selected based on the input of additional data corresponding to the patient's particular limb size and the desired degree of compression corresponding to the limb profile. Both graduated and uniform pressure profiles can be obtained.

What is believed to be a unique method and measuring tape for recording the patient's physical limb size and desired degree of compression for data entry is also disclosed. In addition, the resulting compressive stocking product made according to the invention is believed to provide a novel construction exhibiting a degree of graduated compression and graduated size not heretofore obtained and thus provides a truly customized form of product.

DESCRIPTION OF THE DRAWINGS

FIGS. 3A–3F are fragmentary plan views representing collectively a composite plan view of the front side of a tape devised specifically for use in recording the measurements taken according to FIG. 1 and FIGS. 5–7.

FIG. 15 is a fragmentary perspective view of a revolution sensor for the knitting machine of the invention.

FIG. 16 is a plan view of a rubber, i.e., elastic thread, feed control used in the invention apparatus.

FIG. 17 is a side elevation view of the feed control of FIG. 16.

FIG. 18 is a top plan and somewhat schematic view of the linear lobe cam-gear control arrangement seen in FIG. 17.

FIG. 19 is a fragmentary perspective and schematic view of the main drum rack control used for positioning the elastic thread feed finger under program control according to the invention.

BEST MODE FOR CARRYING OUT THE INVENTION

The method and apparatus of the invention generally lends itself to the manufacture of any type of circular knit goods in which the goods, e.g., a compressive stocking, have either or both the size and degree of compression controlled along the length of the goods. Typical goods to which the invention is expected to be most widely applied are below-knee, above-knee, one-leg-leotard and leotard-type compressive stockings as illustrated in FIGS. 22–25 and in which control of both size and degree of compression are important. A lymphedeme sleeve for a mastectomy patient represents another anticipated application of the invention.

Broadly, as will be seen from later description, the invention makes possible customizing seamless tubular fabric goods to fit a specific body contour and with a specific compression profile fitted to such contour. While primarily directed to seamless tubular fabric goods made from circular knit elastic fabric, such as support stockings, the invention, as seen from later description, also lends itself to some extent to customizing tubular fabric goods formed from flat fabric.

For purposes of explaining the invention, it will be assumed for reference that there is a need for a single, thigh length, compressive stocking graduated in both size and compression along the length of the stocking. The establishment, storing and use of the data to control the circular knitting of such a single compressive stocking will be explained as an example. From this explanation, it will be readily understood how other knit articles can be made according to the invention, such as those illustrated in FIGS. 22-25 and other circular knit tubular goods in which graduated size and compression are desirable features, particularly for therapeutic use.

Figure 2:
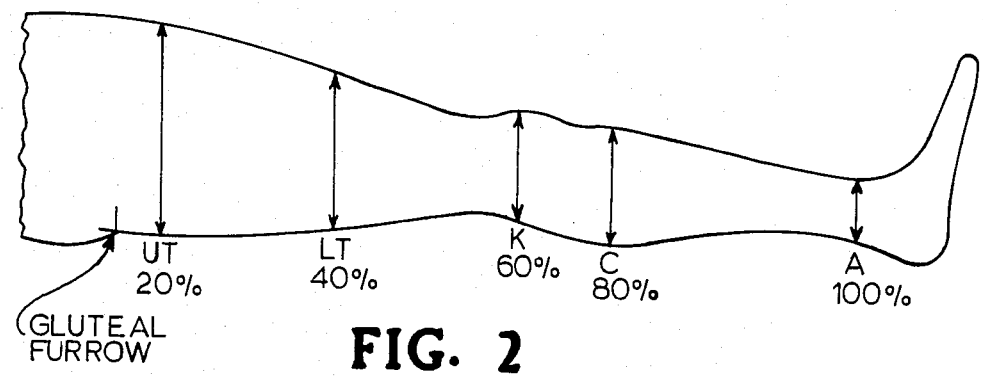
FIG. 2 is a pictorial view of the body portions of FIG. 1 in a supine position with an indication of a typical pressure profile at the points indicated in FIG. 1 using a selected point, the ankle point A being shown by way of example, as the reference point where 100% of the desired pressure is to be applied by way of further example.

In the compression stocking being used by way of example, the stocking is knit so as to provide a graduated pressure profile wherein the pressure exerted on the patient's limb is at a maximum, i.e., 100%, at a selected point, normally the ankle location, and decreases in proportion to the distance from the ankle as further illustrated in FIG. 2. While another reference point and another percentage, other than 100%, could be selected, the stated decrease in pressure from 100% at the ankle follows generally accepted recommendations based on clinical studies set forth in the medical literature or based on physician preference. It has been shown, for example, that certain pressure profiles built into a support stocking are effective in treating certain vascular disorders, including stasis ulcers, varicose veins and swelling of the limb. This form of medical treatment is called compression therapy. The compression therapy begins once a physician determines that a particular patient would benefit from this form of treatment.

It is necessary at the outset that the physician or other trained technician collect accurate leg circumference data on the patient and also determine the pressure profile most beneficial to the patient. A description of this aspect of the invention is next explained.

Figure 1:
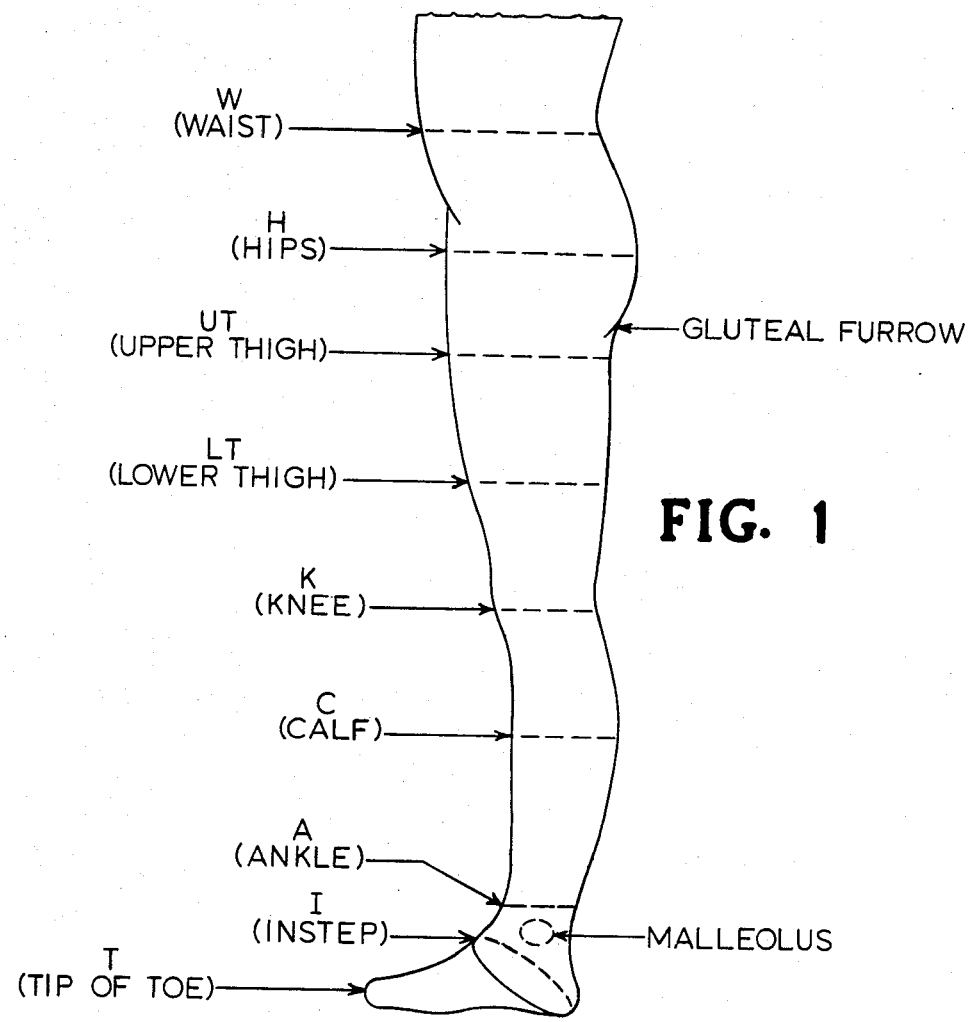
FIG. 1 is a pictorial view illustrating points on the foot, leg, thigh, et cetera, where measurements are taken in the supine position, as in FIG. 5, preparatory to knitting a compressive stocking according to the invention and corresponding to the particular measurements.
Figure 4:
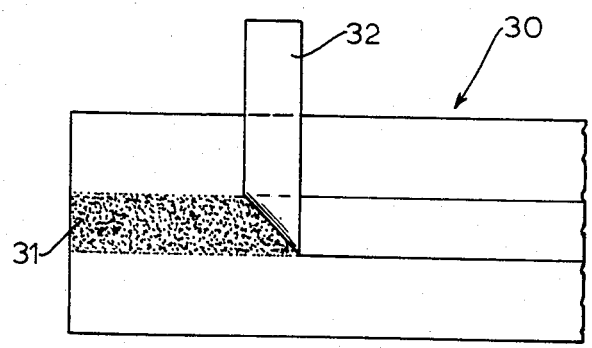
FIG. 4 is a fragmentary plan view of the back side of a portion of the measuring tape shown in FIGS. 3A–3F showing an adhesive strip and removable cover strip provided for the length of the tape on the back side thereof.

As best illustrated in FIG. 1, various portions of the patient's limb and body are designated for reference with letter legends, as for examples W for the waist, H for the hips, UT for the upper thigh, and so forth as further seen in FIG. 1 and various measurements are taken with respect to these portions of the body as later discussed in reference to FIGS. 3A-3F and 5-8. To facilitate the taking and recording of measurements, there is provided an improved measuring tape 30 having printed indicia on the front or face of the tape (FIGS. 3A-3F) and a strip of adhesive material 31 covered by a removable, narrow, paper strip 32 on the back and running lengthwise of the tape 30 (FIG. 4).

Figures 3A, 3B:
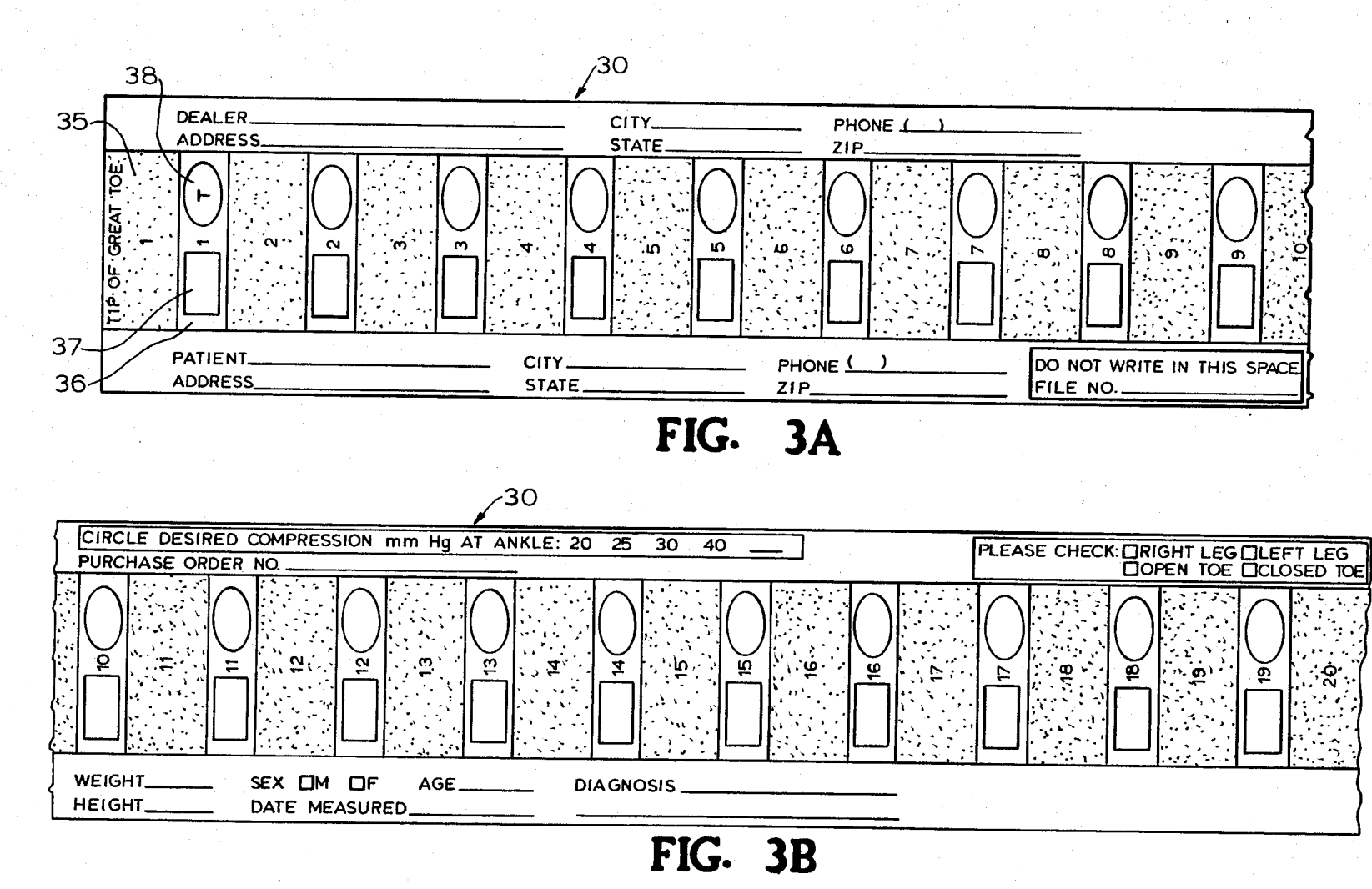
Figures 3C, 3D:
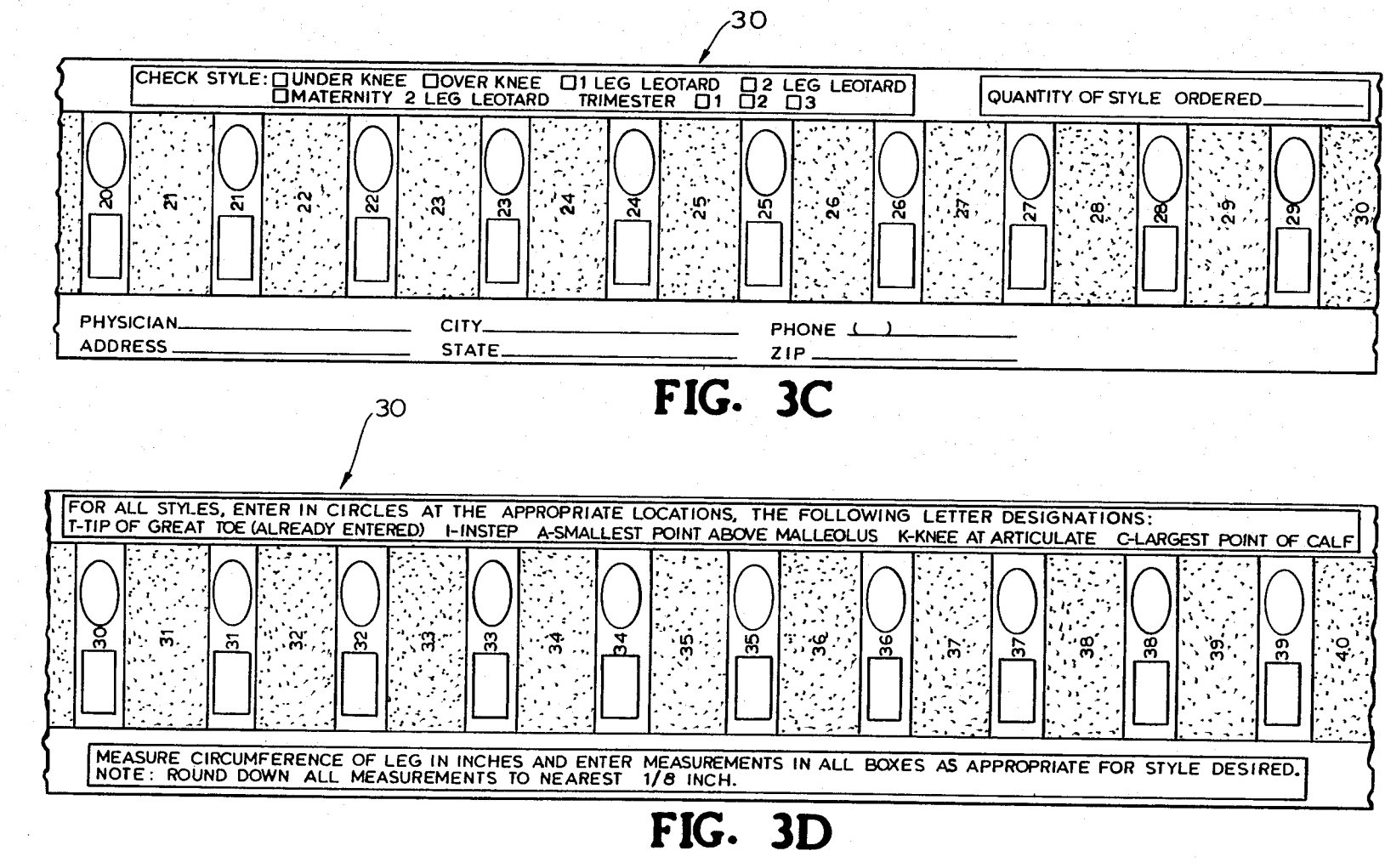
Figure 3E:
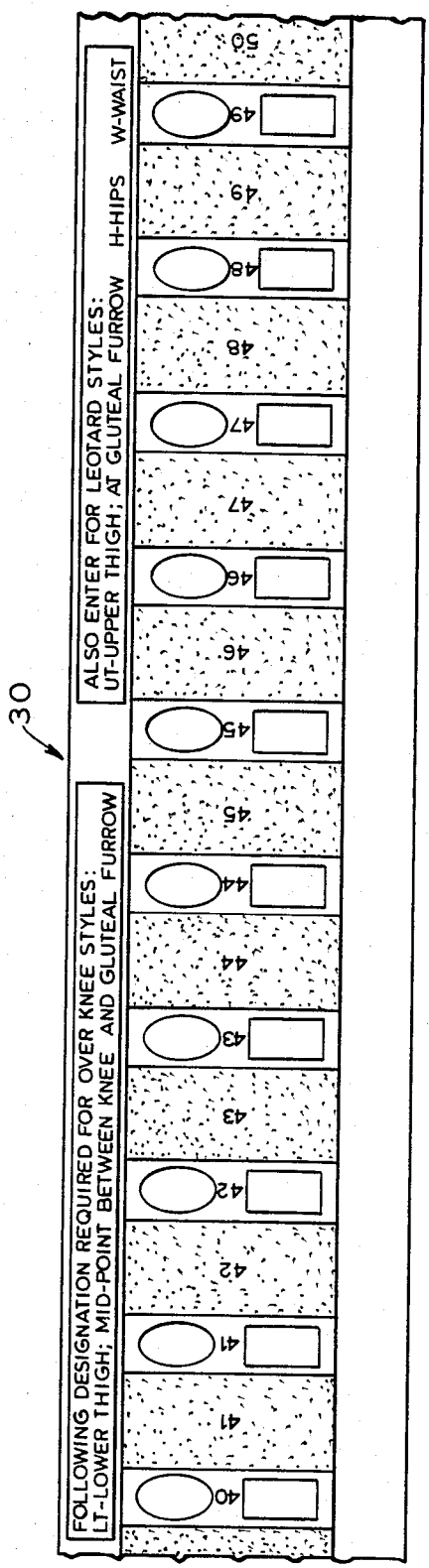
Figure 3F:
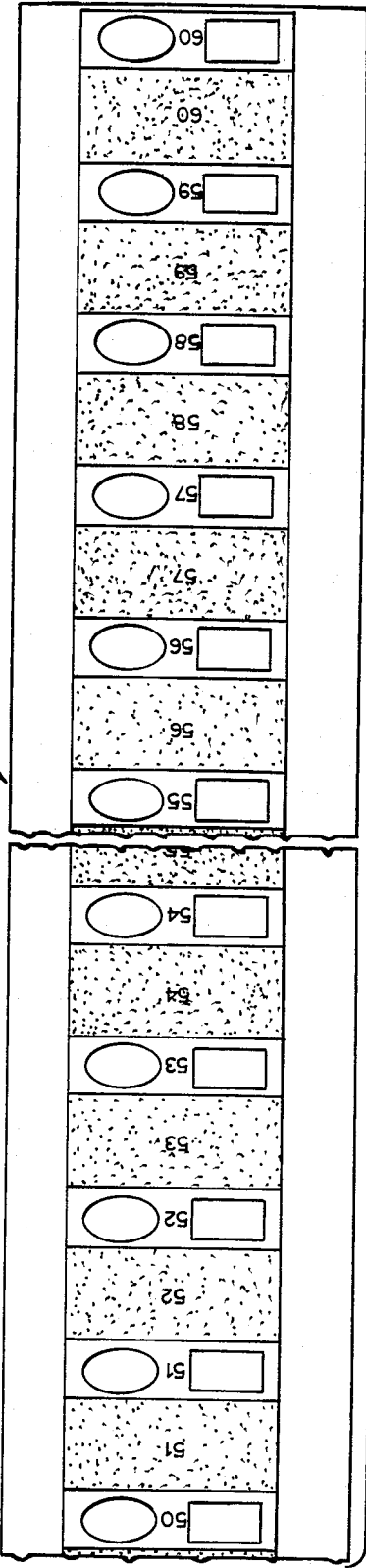

As further illustrated in FIGS. 3A-3F, it will also be noted that tape 30 on its face has a series of printed numbers 1-60 with each number being printed twice. The number is first printed in a shaded box outline, e.g., gray colored box 35 having the number 1 (FIG. 3A), and following this in the lengthwise direction of the tape, the same number is repeated in another smaller, unshaded box outline, e.g., box 36 (FIG. 3A), also having the number 1. In each of the smaller box outlines, it will also be noted that there are printed respective rectangular and elliptical outlines, e.g., outlines 37, 38 (FIG. 3A). As later explained, the rectangular outlines 37 are used for entering dimensions taken and the elliptical outlines are used for entering the respective locations of those body locations or control points corresponding for example to the tip of toe, T (FIGS. 1 and 7), and the like, with the letter T being preprinted as seen in FIG. 3A for establishing a starting position as later explained.

It has also been found desirable to preprint in the margins of tape 30 certain information to be filled in as later discussed and as further illustrated in FIGS. 3A-3F.

Figure 5:
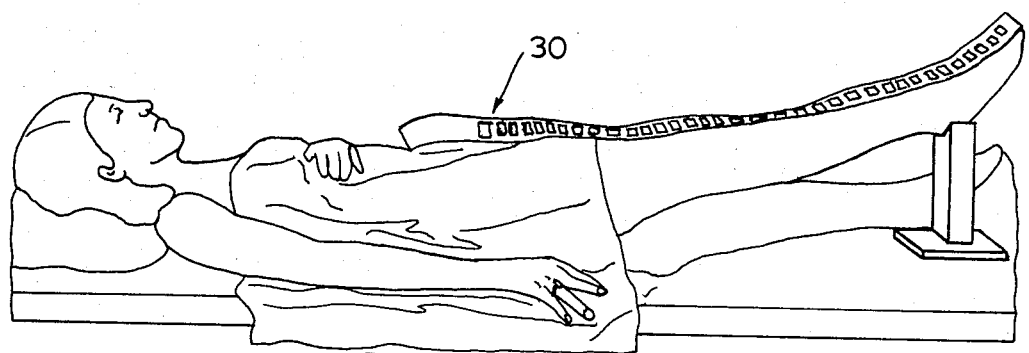
FIG. 5 is a pictorial view of a supine patient in the posture in which measurements are taken according to the invention.

The patient is measured in a supine position as illustrated in FIG. 5 and if hospitalized should be measured in bed before arising in the morning. If this is not possible, the patient should lie at rest in the supine position, with legs slightly elevated for thirty minutes to one hour prior to measurement. Constricting garments should be removed to permit any excess venous buildup in the legs to adequately dissipate.

While the patient is resting preparatory to being measured, the information data to be filled in as illustrated in FIGS. 3A-3F can be completed such as the dealer's name and address, the patient's name and address, the amount of compression, expressed in millimeters of mercury, desired at the ankle in the stocking, stockings or leotards being ordered, the purchase order number, the patient's weight, height, sex, and age and the date on which the measurement is being taken. A brief synopsis of the patient's diagnosis may also be entered with an indication of which leg is being measured, i.e., right or left. If the patient is being measured for a two-leg leotard, for example, a separate information tape 30 will be required for each leg. An indication can also be made as to whether the stocking or leotards being ordered are to be open toe or closed toe, the physician's name and address, the style of garment being ordered and if the patient is pregnant the current stage of pregnancy. Once the foregoing information has been entered on tape 30 and the patient has been positioned as illustrated in FIG. 5, the actual measuring operation can commence.

To initiate the measuring operation, the previously-mentioned adhesive cover strip 32 (FIG. 4) is removed from tape 30 and the patient's foot is positioned at a right angle to the leg so that the toes point up. The end of tape 30 marked "Tip Of Great Toe" (FIG. 3A) is placed so that it is even with the tip of the patient's great toe and is pressed so that the adhesive 31 on the back of tape 30 (FIG. 4) sticks to the toe surface, following which the remaining length of tape 30 is adhered by adhesive strip 31 to the full length of the patient's leg, i.e., up the foot to the ankle, up the shin, over the knee and up the thigh to the full extent of that portion of tape 30 to be used as best seen in FIG. 5.

Figure 6:
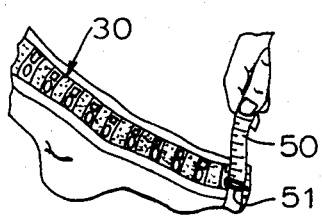
FIG. 6 is a fragmentary pictorial view of a lower foot measurement being taken.
Figure 7:
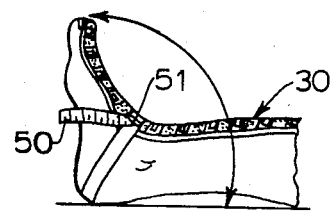
FIG. 7 is a fragmentary pictorial view of an instep measurement being taken.

The measuring tape 50 used for taking measurements should preferably be of the type having a loop 51 as illustrated in FIGS. 6-7. The first measurement is taken by placing an end loop of tape 50 over the end of the patient's foot, as in FIG. 6, so that the measuring tape 50 covers the number 1 gray box, i.e., relatively large rectangular gray outline box 35 on tape 30, as in FIG. 3A, immediately adjacent the legend "Tip of Great Toe". With the measuring tape 50 snug but not tight, the correct measurement is taken at the point at which measuring tape doubles over the top of the loop 51 and is entered in the corresponding smaller size rectangular box 37. A first measurement of 8.5 inches is indicated by way of example in FIG. 8. The letter designations shown in FIGS. 1 and 2 referring to the control measurement points, i.e., T, I, A, C, K, LT, UT, H, and W, are entered in the appropriate elliptical outline box at the appropriate locations as these control or reference measurements are taken. The letter "T" is preprinted in the elliptical outline 38. Measurements are also taken at each inch point between the reference points and are recorded (not shown in FIG. 8) on information tape 30.

After taking the measurement corresponding to reference point T, the next reference measurement point corresponds to the letter "I" for the instep measurement. The instep measurement is taken, as illustrated in FIG. 7, by placing the measuring tape 50 on the particular information tape 30 shaded outline box 52 (FIG. 8) which is located closest to the bend of the foot where the foot starts into the ankle. The measuring tape is looped around the ball of the heel as further illustrated in FIG. 7 and the resultant measurement is recorded in the corresponding rectangular box outline 53 (FIG. 8) with a representative measurement 14.5 inches being indicated in FIG. 8. In a similar manner, other control reference measurements are made at the following points:

A—Smallest point above malleolus.
C—Largest point of calf.
K—Knee at articulate.
LT—Lower thigh at the midpoint between the knee and gluteal furrow.
UT—Upper thigh at the gluteal furrow.
H—Hips.
W—Waist.

Figure 8:
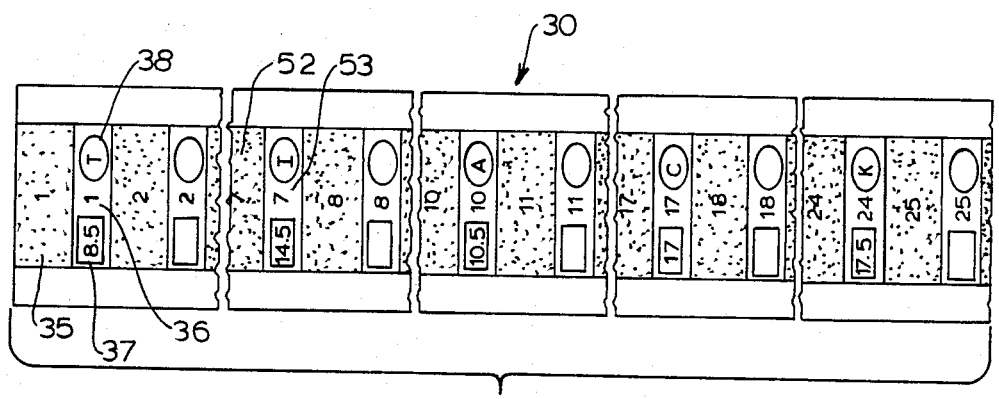
FIG. 8 is a fragmentary plan view of a portion of the tape shown in FIGS. 3A–3F with typical reference location measurements recorded thereon.

At each of the above reference points a measurement will be taken and will be entered in the appropriate small rectangular outline box as well as the appropriate letter or letters in the appropriate elliptical-shaped outline box as further illustrated in FIG. 8. Measurements other than at reference points are entered in the appropriate small rectangular outline box. It may also be noted that some styles of stockings do not require measurement of the entire length of the leg. For example, for an under-the-knee style of stocking (FIG. 22), the measurement can terminate at a point one inch below the bend of the knee. For an over-the-knee style stocking (FIG. 23), the LT (Lower Thigh) measurement will be the top measurement. For leotard styles (FIG. 25), the top measurement will be the W (Waist) measurement.

Figure 10A:
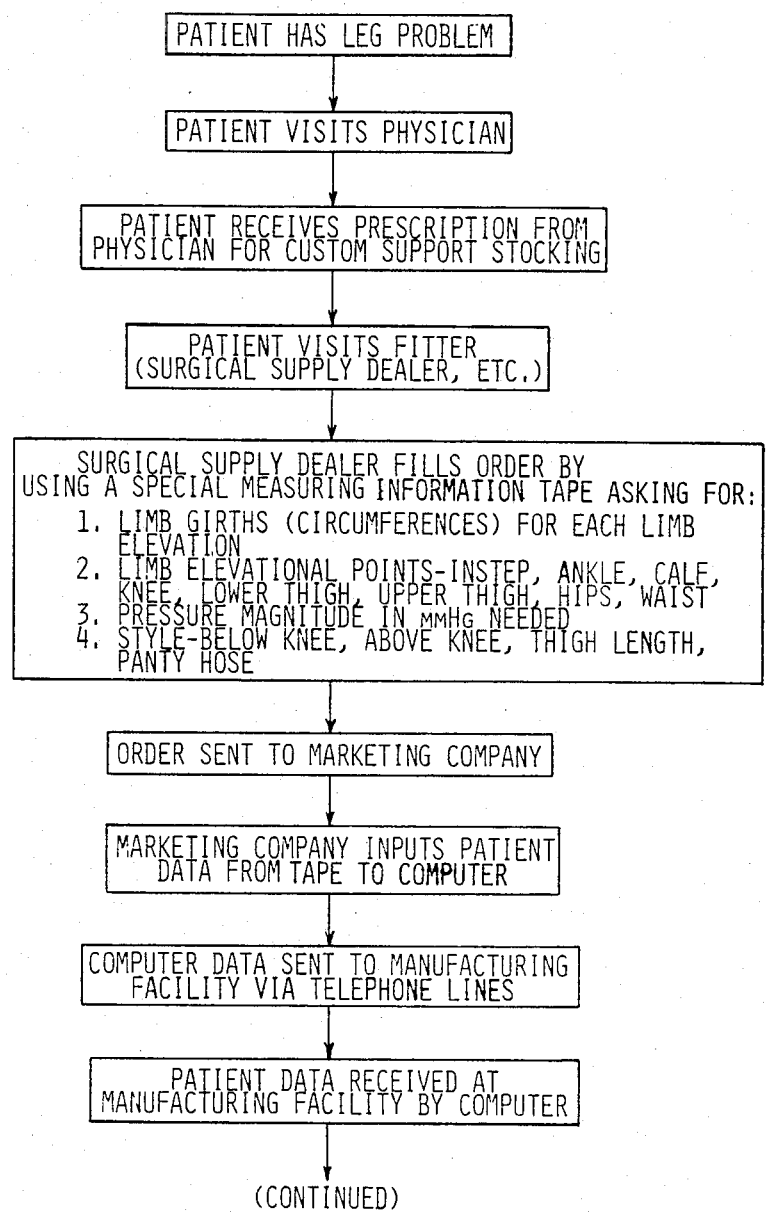
FIGS. 10A, 10B and 10C make up a composite flow diagram of the basic steps associated with the method of the invention.

After the measuring operation has been completed on the patient's leg or legs for the particular style of stocking being ordered, the information tape 30 is removed from the patient's leg and folded so as to cover the adhesive backing material 31 (FIG. 4) and with continued folding as may be necessary to fit the complete tape 30 into an appropriate mailing envelope for mailing to the source of manufacture or to a point at which the patient information can be relayed by telephone or other form of communication to the source of manufacture as illustrated in FIG. 10A. When received at the source of manufacture, such information is preferably received in a form in which it can be immediately stored in memory as part of the control information for controlling the circular knitting machine which will be used to knit the particular customized stocking product according to the specific patient's prescription and needs.

As previously mentioned, the circular knitting machine being used by way of example on which the compressive stocking is to be knit has two variable functions which determine compressive pressure and circumference, namely, cylinder height and the rubber feed speed. The terminology "rubber feed" is typically used to mean the mechanism for feeding the elastomeric threads whether in the nature of rubber, Spandex, or the like. These functions are controlled by means of later-explained computer-controlled electromechanical air cylinder-actuated racking devices (FIGS. 16–21) with the cylinder height having in the example used for illustration twelve possible positions and the rubber feed in the same example having forty possible speed positions so as to produce at one extreme a relatively loose fabric with low compression as in FIG. 13 or at the other extreme a relatively tight fabric with high compression as in FIG. 14 as well as graduated variations thereof. While in the illustrative construction shown in FIG. 13, one rubber, e.g., Spandex, thread is knit in and another rubber thread is laid in as illustrated, those skilled in the art will readily appreciate that there are numerous other constructions suited to the invention.

In the example chosen for illustration, the twelve cylinder heights and forty rubber feed speeds thus allow for the possibility for 480 different combinations of machine settings. Each possible combination of machine settings, to the extent practical, is used to produce a test sample of fabric. In some instances, it has not been practical to knit a sample because of machine limitations related to the particular combination of machine settings. In any event, except for those instances in which the combination of machine settings were impractical to use for knitting the test sample, all of the possible 480 separate samples of fabric were knit and tested to derive the size and pressure information used in conjunction with a software program to decide and select the specific machine settings, i.e., cylinder height and rubber feed speed, to be used in various portions of the stocking to be knit as further illustrated in FIGS. 10B and 11.

The fabric samples as well as the compressive stocking being used by way of example were all knit on a multi-feed circular knitting hosiery machine with one elastic thread lay-in feed and using a 3¾ inch diameter cylinder. It has been found that the majority of patients in need of a compressive-type stocking will have measured circumferences falling within a range of 5.5 inches minimum to 49 inches maximum. With this limitation in mind, the sample fabric data base was developed with the further objective of being able to knit fabric exhibiting a sufficient number of different stretched circumferences at ⅛ inch increments to meet the full range of patient limb sizes and compression needs contemplated to be experienced in utilizing the invention. Considering that in various portions of the compressive stocking product the stretched circumference may be held at some fixed value for some number of courses exceeding ⅛ inch in width, the invention data base was built up with the choice of being able to obtain 348 different possible stretched circumferences between a minimum of 5.5 inches and a maximum of 49 inches.

Figure 9:
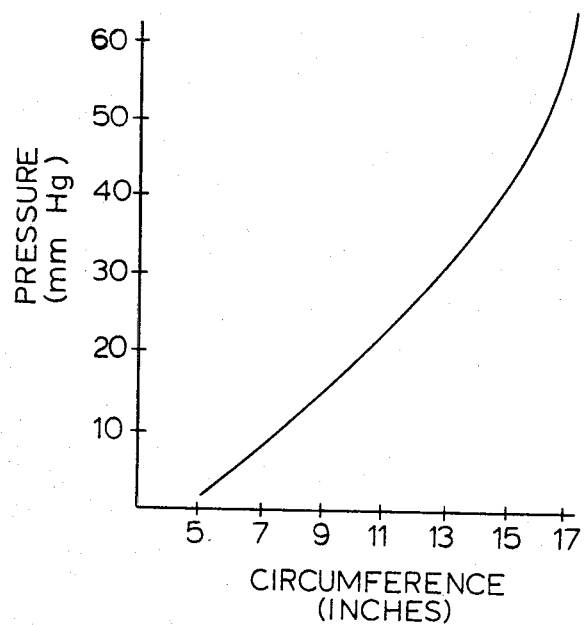
FIG. 9 is a typical modulus of elasticity curve as obtained from measuring a sample fabric tube for establishing a data base according to the invention.

The mentioned fabric samples after being fabricated were tested for pressure using a tensile testing device and the test on each sample was performed at circumferences which varied from the sample's limp width up to its dead stretch. The "reconstruction square" technique was employed, in which a 2"×2" square was stretched to simulate an actual wear condition. Each sample was tested for the pressure provided at ten intermediate, equally-spaced stretched circumferences between the limp width and the dead stretch. The ten intermediate test positions plus the limp width and dead stretch positions thus provided twelve different circumference test points for each sample. The twelve test points were then used to generate a modulus of elasticity curve for that particular sample. An example of this type of curve is shown in FIG. 9.

Figure 11:
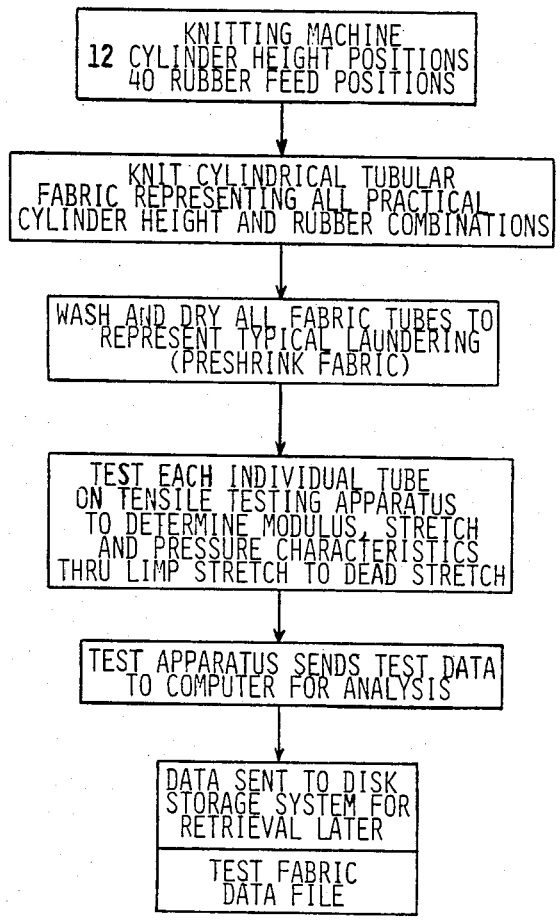
FIG. 11 is a flow diagram indicating the manner in which a data bank is established for providing a large number of possible stocking size and compression possibilities related to specific combinations of cylinder height and rubber feed positions.

The testing of the twelve data points by the tensile tester was monitored by computer, as diagrammatically illustrated in FIG. 11, with a statistical analysis program to provide a fifth-degree polynomial equation with pressure as the dependent variable and circumference as the independent variable and of the form $$y = c_0 + c_1 x + c_2 x^2 + c_3 x^3 + c_4 x^4 + c_5 x^5$$

where y is the pressure, $c_n$ are constants, and $x^n$ are powers of x, where x is the circumference, and n ranges from 0 to 5. This equation allows the collected data to be stored in a highly condensed form and also allows a prediction of the pressure at any point within the stretch capability of the test sample. The twelve circumference test points with their corresponding pressures thus comprise 24 data variables for each sample. The fifth-degree equation allows the same information to be stored as a constant plus the multiplicative constants of the five powers of the circumference variable. The reduction of 24 pieces of data into six constants provides a substantial savings in the computer memory requirement as well as allowing an accurate prediction of the pressure at any point along the test sample modulus curve.

To determine the pressure at a given stretch circumference, from limp to dead stretch, for a specific test sample, the constants are called from the computer memory, the circumference and its required powers are input into the equation, the proper mathematical operations are performed, and the predicted pressure is obtained. It has been found that the predicted pressure based on the polynomial equation achieves an accuracy to within one part in 200 as compared to the actual pressure as determined on the tensile tester.

Once the polynomial pressure equations were developed for each of the different test samples, the equations were used to generate tables to indicate the pressure, expressed in millimeters of mercury, provided by a particular machine setting (i.e., the combination of cylinder height and rubber feed speed) at a particular circumference. An example table is shown as follows for a stretched circumference of 13.375 inches. Each pressure reflected in the example table was taken from a different sample. For example, at rubber feed setting 5, cylinder height setting 4, the indicated pressure of 39.9 was obtained, for example, from one of the 480 samples. Such a circumference table was prepared for each of the 348 stretched circumferences.

| CIRCUMFERENCE = 13.375 Inches Pressure in MM-HG as a Function of Machine Setting Smoothed Pressure-Circumference Grid | | | | | | | | | |
|---|---|---|---|---|---|---|---|---|---|
| | CYLINDER HEIGHT | | | | | | | | |
| | 1 | 2 | 3 | 4 | ... | 9 | 10 | 11 | 12 |
| RUBBER FEED | | | | | | | | | |
| 1 | 0.0 | 0.0 | 0.0 | 0.0 | ... | 0.0 | 0.0 | 0.0 | 0.0 |
| 2 | 0.0 | 0.0 | 0.0 | 0.0 | ... | 0.0 | 0.0 | 0.0 | 0.0 |
| 3 | 0.0 | 0.0 | 42.4 | 40.5 | ... | 30.7 | 28.8 | 26.9 | 0.0 |
| 4 | 0.0 | 0.0 | 41.7 | 39.7 | ... | 30.0 | 28.1 | 26.1 | 0.0 |
| 5 | 44.8 | 42.9 | 40.9 | 39.9 | ... | 29.3 | 27.3 | 25.4 | 23.4 |
| 6 | 44.1 | 42.1 | 40.2 | 38.3 | ... | 28.5 | 26.6 | 24.6 | 22.7 |
| 7 | 43.4 | 41.4 | 39.5 | 37.5 | ... | 27.8 | 25.8 | 23.9 | 22.0 |
| 8 | 42.6 | 40.7 | 38.7 | 36.8 | ... | 27.1 | 25.1 | 23.2 | 21.2 |
| 9 | 41.9 | 39.9 | 38.0 | 36.0 | ... | 26.3 | 24.4 | 22.4 | 20.5 |
| 10 | 41.1 | 39.2 | 37.2 | 35.3 | ... | 25.6 | 23.6 | 21.7 | 19.7 |
| . | | | | | | | | | |
| . | | | | | | | | | |
| 33 | 24.1 | 22.2 | 20.3 | 18.3 | ... | 8.6 | 6.6 | 4.7 | 2.7 |
| 34 | 23.4 | 21.5 | 19.5 | 17.6 | ... | 7.8 | 5.9 | 4.0 | 2.0 |
| 35 | 22.7 | 20.7 | 18.8 | 16.8 | ... | 7.1 | 5.2 | 3.2 | 1.3 |
| 36 | 0.0 | 20.0 | 18.0 | 16.1 | ... | 6.4 | 4.4 | 2.5 | 0.5 |
| 37 | 0.0 | 19.2 | 17.3 | 15.4 | ... | 5.6 | 3.7 | 1.7 | 0.0 |
| 38 | 0.0 | 18.5 | 16.6 | 14.6 | ... | 4.9 | 2.9 | 0.0 | 0.0 |
| 39 | 0.0 | 0.0 | 15.7 | 13.8 | ... | 4.2 | 2.2 | 0.0 | 0.0 |
| 40 | 0.0 | 0.0 | 15.1 | 13.1 | ... | 0.0 | 0.0 | 0.0 | 0.0 |

-continued (CIRCUMFERENCE = 13.375 Inches Pressure in MM-HG as a Function of Machine Setting Smoothed Pressure-Circumference Grid)

The pressure, in millimeters of mercury, that a particular combination of machine settings will provide can be determined from the table. No entry in the table indicates that no sample could be knit at that particular machine setting for the circumference on which the table is based. The minimum and maximum circumferences are restricted, respectively, to the test sample limp width and dead stretch. Some possible circumferences may be smaller than the sample limp width, while other circumferences are greater than the dead stretch of the sample. For these conditions, there will be no entry in the table. As previously mentioned, applicants have found that, with few exceptions, leg circumferences range from a minimum of 5.5 inches up to a maximum of 49 inches. These values are the limits placed on the circumference range of the type of compressive stocking made according to the invention. Pressure grid tables described above were generated for all values of circumference from 5.5 inches up to 49 inches in $\frac{1}{8}$ inch increments, for a total of 348 separate pressure grid tables. These 348 separate pressure grid tables constitute the data from which the machine settings are selected to satisfy the physician's pressure and circumference criteria coordinated with the patient's actual physical measurements taken as previously explained.

As previously described, the physician or a designated assistant collects circumference data on a particular patient and determines the pressure profile he requires in the stocking. By pressure profile is meant the pressure exerted at the five leg locations or reference points indicated in FIGS. 1 and 2. The pressure exerted at these locations or points, other than the ankle, is referenced to the pressure at the patient's ankle and is given as a percentage of the ankle pressure. A reference location other than the ankle could, of course, be selected. Based on clinical studies, a standard pressure profile has been determined which has been shown to be beneficial to a majority of the patients who use compression therapy. Referenced to the specified ankle pressure, the standard pressure profile is: calf (C), 80% ankle pressure; knee (K), 60% ankle pressure; lower thigh (LT), 40% ankle pressure; and upper thigh (UT), 20% ankle pressure. These percentages for the standard pressure profile are indicated in FIG. 2. By selecting the standard pressure profile, the physician only has to determine the ankle pressure for the patient's stocking and selects such ankle pressure based on the particular patient's need and customary pressure for such need and which is entered on tape 30 by circling the appropriate pressure indicated in FIG. 3B.

Figure 10B:
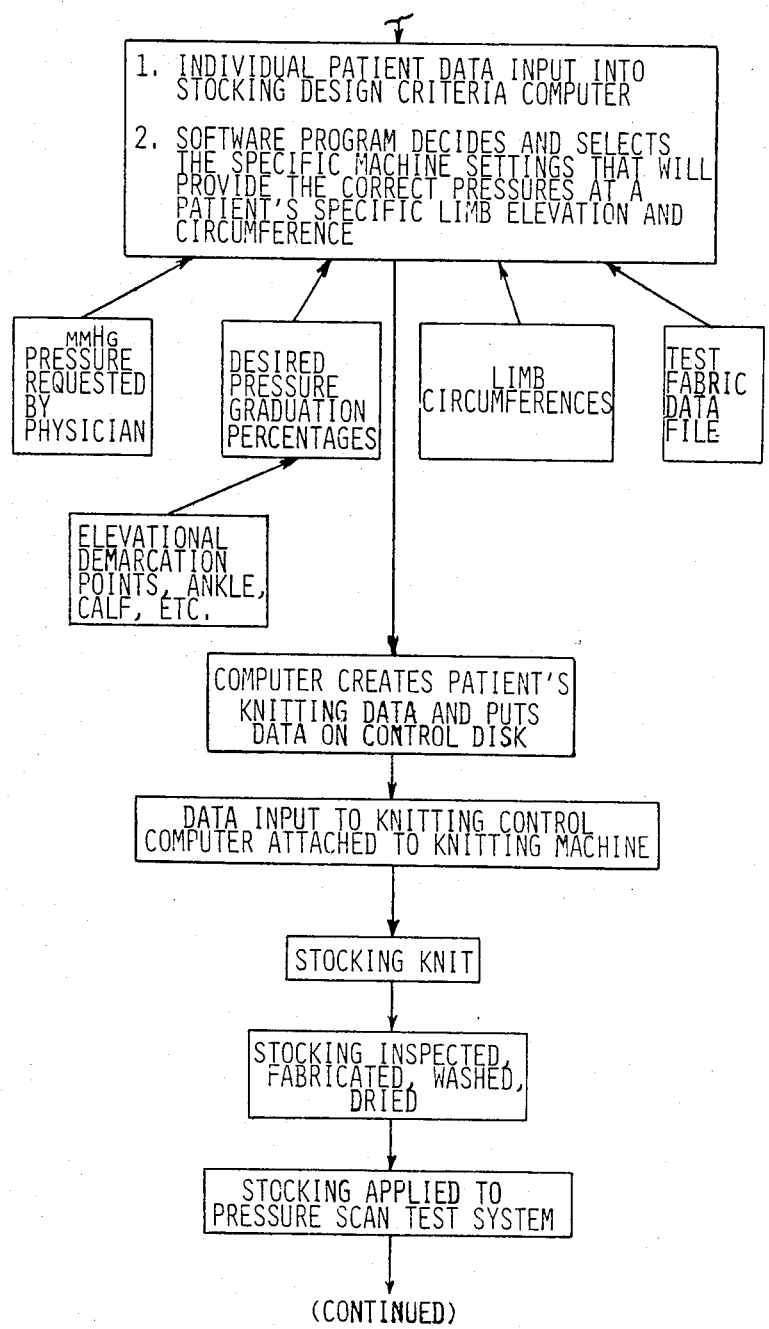
Figure 10C:
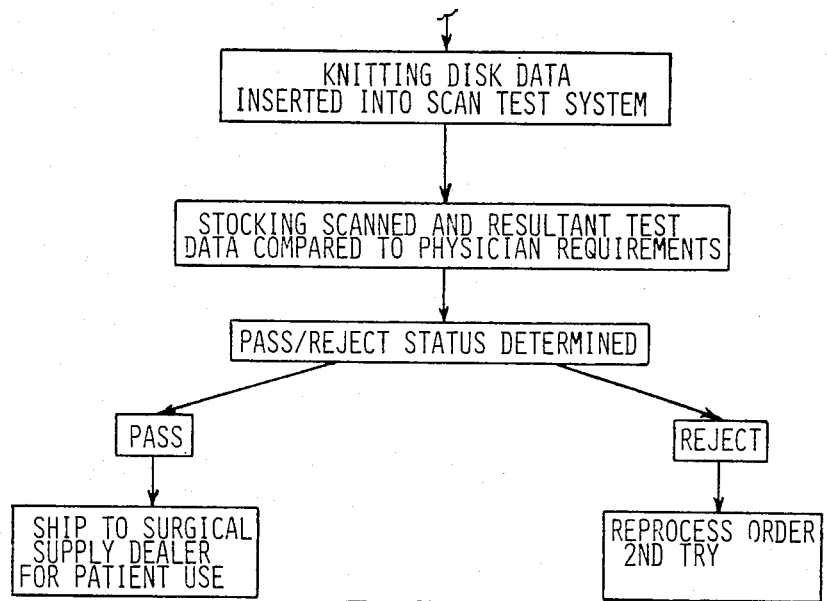
Figure 12:
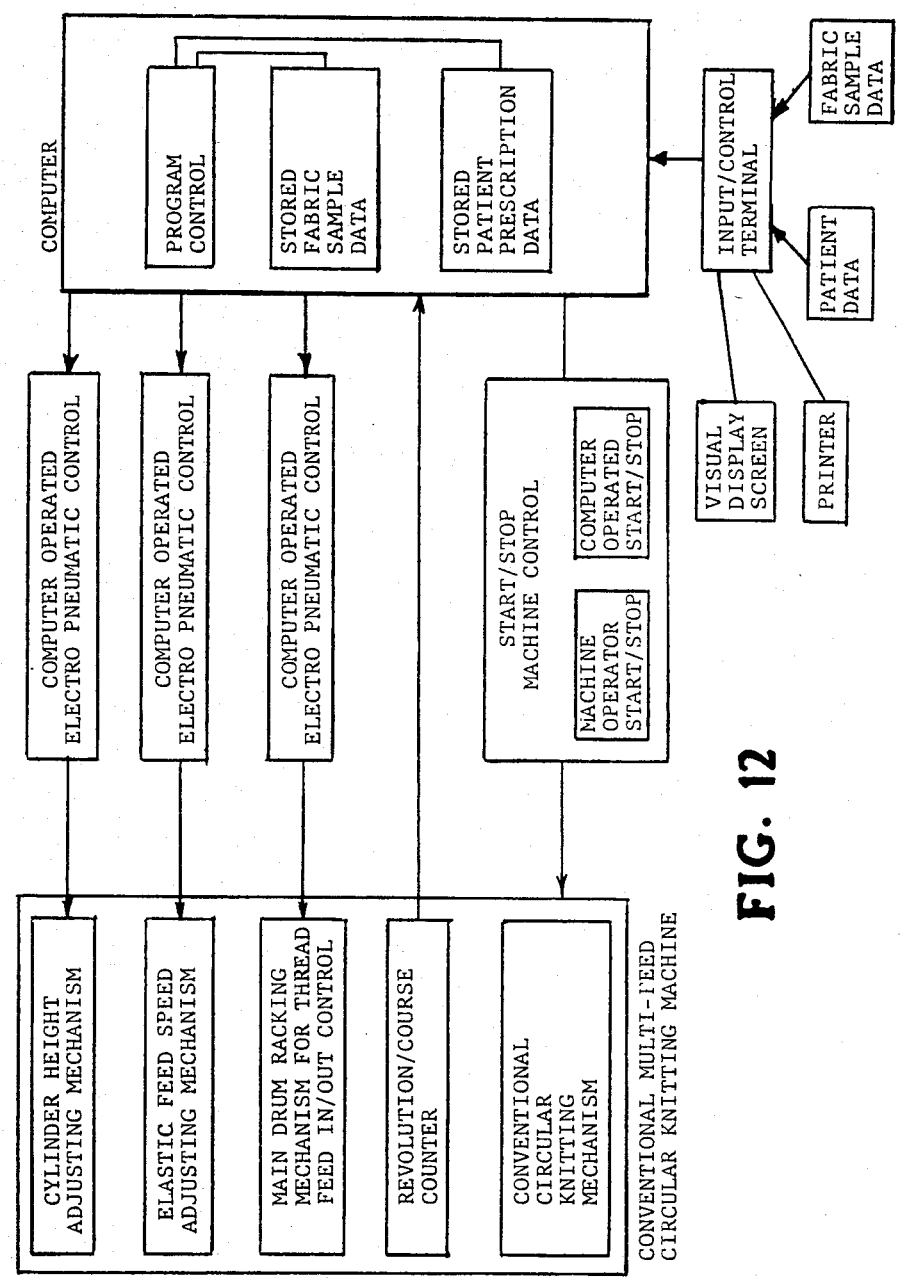
FIG. 12 is a schematic diagram of an overall system according to the method and apparatus of the invention.

Once the physician's data has been generated, it is entered into the computer memory for processing either through an operator terminal, through telephone wire communication, or the like as diagrammatically illustrated in FIGS. 10A, 10B and 12. Utilizing an appropriate software program, the computer uses the pressure profile to determine the pressure required at each leg circumference point. Such pressures are selected so as to provide a smooth, graduated transition, inch for inch, in pressure from the ankle, through each leg segment point, up to the gluteal furrow. In addition, the pressures determined by the computer software also satisfy the physician-specified pressure profile. For each leg circumference point, a machine setting is determined which provides the required pressure and circumference. The computer accesses the pressure grid table for the circumference point under consideration and searches for the required pressure. Once this pressure is found, the machine settings which provide this pressure or the closest approximate pressure are read from the grid table and stored in memory. Typically, several combinations of machine settings will be found that provide the necessary pressure. Thus, an optimizing routine is built into the software such that the combination of machine settings which will provide the smoothest transition in machine setting change from each successive, previously-determined leg circumference point is selected. Preferably each of the 40 increments of yarn feed speed change results in a smaller change in pressure of a stocking than does each of the 12 increments of cylinder height change. Therefore, the optimizing routine maintains cylinder height constant for at least one inch as machine limitations will allow but changes yarn feed speed more frequently.

The process of machine setting determination progresses from the ankle, through each leg circumference point, at one-inch intervals, up to the gluteal furrow. Once these settings are determined and stored, the settings for the foot and, if applicable, the panty regions of the stocking are determined. The settings for these regions are based respectively on the size of the patient's foot and the circumference of his waist. The foot size or foot value placed in memory is determined by the I measurement (FIGS. 1 and 5) so as to provide for small, medium or large foot size. These machine settings are stored in the computer memory along with the machine settings for the graduated pressure, leg region of the stocking. All of the machine settings necessary to knit the customized support stocking of the invention are thus stored in the computer which is to be used for controlling the circular knitting machine during actual knitting of the desired compressive stocking being used by way of example.

As an example of the type information stored and used for control of the knitting operation, the following table of values represent typical values employed for knitting for a female patient, a leotard style stocking having a closed toe and a desired ankle pressure of 28 mmHg. Other information related to gluteal furrow to waist length and crotch piece size were also obtained but are not deemed necessary for an understanding of the invention. With this background in mind, the following information was collected, stored, analyzed and used to produce the control settings indicated for the type of foot (T) to upper thigh (UT) portions of the stocking. Since the instep measured (I) as analyzed by the program was indicated to be for a small foot, the appropriate cylinder height setting 5 and rubber feed speed setting 8 for points 1-7 were selected by the computer program and employed during knitting for this portion of the stocking. Target pressures for points 8-34 were also computed for comparison with the listed actual pressures taken from the circumference of tables previously referred to. The lay-in Spandex ended at point 31 and points 32-34 were achieved with an insert.

TABLE

| LEG POSITION | LOC. POINT | LEG GIRTH (INCH) | ACTUAL PRESS mm-Hg | PERCENT OF MD'S ANKLE PRESSURE | SETTING SELECTED CYLINDER HEIGHT | RUBBER FEED |
|---|---|---|---|---|---|---|
| TIP OF FOOT | PT#1 | 6.50 | | | | |
| | PT#2 | 7.50 | | | | |
| | PT#3 | 8.25 | | | | |
| | PT#4 | 8.50 | | | | |
| | PT#5 | 9.00 | | | | |
| HEEL-INSTEP | PT#6 | 11.88 | | | SMALL FOOT | |
| | PT#7 | 8.75 | | | 5 | 8 |
| ANKLE | PT#8 | 8.38 | 28.6 | 100 | 1 | 4 |
| | PT#9 | 8.50 | 27.8 | | 1 | 5 |
| | PT#10 | 9.50 | 27.7 | | 1 | 7 |
| | PT#11 | 10.13 | 27.1 | | 1 | 9 |
| | PT#12 | 11.00 | 26.2 | | 1 | 12 |
| | PT#13 | 11.63 | 25.6 | | 1 | 15 |
| | PT#14 | 12.50 | 25.0 | | 1 | 20 |
| | PT#15 | 13.38 | 24.3 | | 1 | 26 |
| | PT#16 | 13.88 | 24.0 | | 1 | 30 |
| CALF | PT#17 | 13.88 | 23.2 | 80 | 1 | 31 |
| | PT#18 | 13.75 | 21.8 | | 1 | 32 |
| | PT#19 | 13.50 | 20.5 | | 1 | 32 |
| | PT#20 | 13.25 | 18.6 | | 1 | 33 |
| KNEE | PT#21 | 13.63 | 17.5 | 60 | 2 | 34 |
| | PT#22 | 14.63 | 16.4 | | 4 | 33 |
| | PT#23 | 15.13 | 15.3 | | 5 | 33 |
| | PT#24 | 15.88 | 14.9 | | 6 | 32 |
| | PT#25 | 16.50 | 13.9 | | 7 | 32 |
| | PT#26 | 17.38 | 12.9 | | 8 | 33 |
| MID THIGH | PT#27 | 18.00 | 12.1 | 40 | 9 | 32 |
| | PT#28 | 18.88 | 11.3 | | 10 | 32 |
| | PT#29 | 19.00 | 10.4 | | 11 | 30 |
| | PT#30 | 19.63 | 9.8 | | 12 | 29 |
| | PT#31 | 20.00 | 9.0 | | 12 | 32 |
| | PT#32 | 20.38 | 7.9 | | 8 | 32 |
| | PT#33 | 20.63 | 6.7 | | 8 | 32 |
| UP. THIGHT | PT#34 | 22.25 | 5.6 | 20 | 8 | 32 |

As previously described, the computation of machine settings is made upwardly, i.e., from toe to welt, whereas the knitting is downwardly, i.e., from welt to toe. This allows the welts to be made on the machine.

The knitting of the stocking is a control operation during which the computer controls the cylinder position and rubber feed speed as a means of achieving the desired pressure profile, graduated pressures and circumference sizes corresponding to the physician-submitted data for the particular patient's stocking being knit. The knitting process begins at the top or waist region of the stocking, depending on the style being knit and proceeds through the graduated pressure leg region down to the tip of the foot. Throughout the knitting process, the computer controls the cylinder height position and the rubber feed speed of the knitting machine to provide a final product which meets the physician-specified criteria and offers a medically-correct, graduated pressure, support stocking for the patient.

While known programming procedures provide a variety of forms in which the knitting control information may be stored, analyzed, recovered from memory, selected, and the like, certain practical considerations are mentioned based on use of the invention. The invention program operates such that the stocking is typically started with the lowest possible cylinder height position, and the slowest possible rubber feed speed, i.e., the tight stitch positions. The program also calls for the cylinder height to be selected not more than once per inch whereas the rubber feed speed is selected each four revolutions of the knitting cylinder as determined by the revolution course counter mechanism shown in FIG. 15 and later described. In selecting machine settings, the computer program is organized so as to first select target pressures at the key points, i.e., locations A, C, K, LT, and UT. Pressures at the intervening inch points are next selected. Machine settings are then determined keeping the cylinder height constant where possible and making only those changes in machine settings required to produce a smooth transition. Program commands can, of course, be delivered substantially instantaneously whereas mechanical execution of such commands takes time. In any event, changes in machine settings, whether for rubber feed, cylinder height, or both, are executed at evenly spaced intervals between the inch points. Thus, depending on the change in settings in going from one inch point to another inch point, the inch interval therebetween might be effectively divided by the computer once, twice or three times so that changes in the settings take place once, twice or three times in going from one inch point to the next. Execution of the mechanical commands are thus smoothed when implemented with the machine limitations programmed in. In general, it has been found desirable to minimize cylinder height changes and minimize rubber feed changes throughout execution of the knitting program for a particular stocking. The I, i.e., instep, value arbitrarily determines a foot value, i.e., small, medium, large, etc., which is used as a reference for knitting the foot portion of the stocking and which thereby controls the foot pressure. Within the scope of the invention, other measurements could be employed to obtain a more specific and graduated pressure profile in the foot portion of the stocking. However, in actual practice, the obtaining of a graduated pressure profile is normally deemed more important from the ankle location upwardly. Where applicable, the W, waist measurement, determines the panty size. Waist pressure is normally not critical. Thus, the waist or panty portion is primarily knit with the objective of obtaining a good fit.

Figure 27:
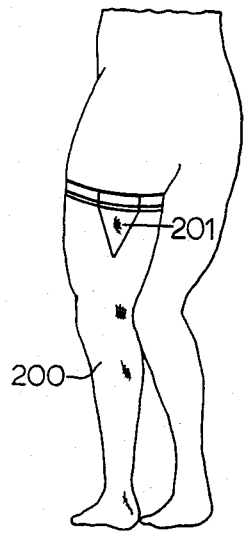
FIG. 27 illustrates a patient having an abnormally large upper thigh fitted with a compressive stocking having a triangular-shaped insert to produce a stocking for the patient's needs but beyond the knitting capability of the machine for such upper thigh circumference.
Figure 24:
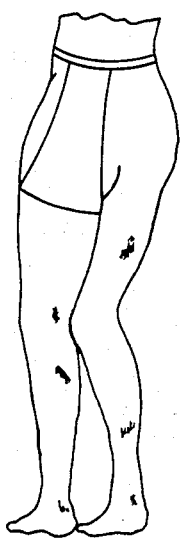
Figure 26:
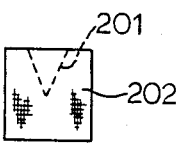
FIG. 26 schematically represents a rectangular-shaped test fabric sample from which a triangular insert, shown in dashed lines, is cut for installing in the stocking of FIG. 27.
Figure 25:
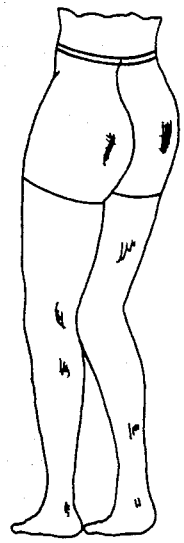

Whatever size knitting machine is selected, such machine can only knit a fabric of some maximum stretched width. Therefore, where a patient's thigh measurement, for example, exceeds the machine's capability, a method has been developed for sewing in the stocking 200 a triangular panel 201 in the upper thigh region as illustrated in FIG. 27. However, prior to cutting and sewing in such panel 201, a data file is made up by forming and tensile testing a range of rectangular-shaped fabric samples, made up with a wide range of cylinder height-rubber feed setting combinations, such as representative sample 202, shown in FIG. 26, from which the desired triangular panel 201 is cut. Such tests provide the compression characteristics of the fabric samples thereby enabling a computer determination of which sample is best suited so that after the triangular insert is seamed in placed as in FIG. 27, the desired compressive characteristics in the upper thigh region will be both known and achieved in practice in the finished product. In practice, a panty-type fabric having a knit in elastic yarn alternating with a non-elastic yarn is preferred for the inserts. Thus, a wide range of machine settings were employed to build up a range of panty hose fabric samples which after being tested provided a wide range of compression-circumferences combinations from which an optimized selection of a particular fabric sample can be designated by computer program from the test fabric data file. The end result is that even though the patient may have an unusually large upper thigh, and even though the circular knitting machine lacks the capability of knitting tubular fabric to accommodate to such patient in such region, the invention nevertheless provides a method by which the resulting stocking 200 with the insert 201, does meet the objective of achieving a predetermined pressure profile in such upper thigh region even though substantially larger than normal.

As previously mentioned and as schematically illustrated in FIG. 12, three mechanisms on the circular knitting machine are under program control. These mechanisms include the rubber feed speed control, the in/out thread finger-drum racking control and the cylinder height control. Means are also provided whereby the knitting cylinder revolutions are counted and the count fed to the computer as electrical signals thereby enabling the course count to control the timing of operating the various program controlled mechanisms on the machine. Additionlly, as shown in FIG. 12, means are provided whereby the computer can visually signal to the machine operator by a screen message when the knitting operation is ready to commence under program control. This mode of operation allows the operator to observe the screen visually for the appropriate message, e.g., "Now Ready To Start", or the like, so as to manually start the machine and also manually stop the machine on completion of the stocking. Alternatively, both stopping and starting of the machine as well as control of the machine during knitting can be performed through the computer under program control.

Since the general art of computers and programming of the type suited to the invention are known and since mechanisms for adjusting cylinder height and rubber feed speed and racking the drum to control thread finger positions are all old and well known, per se, as well as means for counting knitting cylinder revolutions and for starting and stopping the machine are all well known, the description will primarily direct itself to the general construction of these mechanisms and how they adapt for program control. The reader should also bear in mind that a conventional circular hosiery knitting machine is used by way of example and reference, the particular machine employed being equipped with two body yarn feeds, one lay-in elastic feed and a three and three-fourths inch cylinder.

The mechanism for revolution counting, i.e., course counting, is illustrated in FIG. 15 in which the main shaft 70, left clutch pinion 71 and right clutch pinion 72 are shown for reference. For purposes of counting each revolution of main shaft 70, corresponding to each rotation of the knitting cylinder and also to each course formed, there is provided a reflective surface 73 and a photo light source-detector 74 with connecting leads 75. As will be readily understood, detector 74 produces a pulse signal for each revolution and thus provides a means for counting the number of cylinder revolutions and courses knit and developing processible signals related thereto.

The elastic or so-called rubber feed speed control is somewhat schematically illustrated in FIGS. 16–18 in which the elastic, for example Spandex, thread 78 is fed between the supply spool 80 and a driven roll 81. Thread 78 after leaving roll 81 is fed through a suitable guide or guides 82 and through a feed finger 84 to the needle circle 83. Roll 81 is mounted on driven shaft 85 which in turn is driven by a rubber tired wheel 86. Wheel 86 is loaded by compression spring 88 and has a suitable slidable, spline connection, not shown, to shaft 85 such that wheel 86 can both revolve with and slide lengthwise of shaft 85. Wheel 86 is in turn held in constant contact with a drive disc 90 driven at a constant speed off the main drive shaft by a drive shaft 91. Rubber feed speed is effectively controlled by controlling the radial position of wheel 86 with respect to disc 90. Thus, the further wheel 86 moves out from the center of disc 90, the faster wheel 86 turns and thus the faster drive roll 81 turns whereby to achieve a faster rubber speed. However, as wheel 86 moves closer to the center of disc 90, the rubber feed speed reduces and reaches a minimum when wheel 86 is centered over the center of disc 90.

A choice of 40 rubber speeds is provided by means of a bidirectional racking gear set 100 made up of gears 105, 106 each having 40 teeth and thus 40 possible positions. The gear set 100 is positioned bidirectionally by means of air solenoids 101, 102 controlled by a respective pair of electrically-controlled solenoid valves 103, 104 connected through a suitable controller 108 to the computer 110. Racking of gear set 100 bidirectionally causes the associated linear lobe cam 115 secured to gear set 100 to move in equal, corresponding bidirectional rotational increments and thereby raise and lower cam follower arm 120 accordingly. Use of a linear lobe cam facilitates use of program control to obtain uniform mechanical responses to computer commands and thus a smooth mechanical transition from change to change. Arm 120 is connected to and positions rod 121 and in turn a bell crank arrangement comprising arms 126, 127. Motion of arm 127 back and forth thus causes wheel 86 to move in and out on disc 90 and thereby control the speed at which the elastic thread 78 is fed to the needles during those portions of the stocking in which elastic thread is employed for its desired compressive and therapeutic effect.

In operation the desired elastic thread feed is selected by the computer program for each portion of the stocking where elastic thread is used in conjunction with a selected cylinder height position for the same portion so as to obtain the desired circumference and pressure for that particular portion of the stocking. As the knitting operation proceeds through the various portions of the stocking, other rubber feed speed-cylinder height combinations are automatically fed to the controller 108 under program control for knitting the various portions of the stocking comprising the entire stocking construction. Selection of the rubber feed speed is thus effectively accomplished by selectively energizing either air cylinder 101 or air cylinder 102 according to whether rubber feed speed is to be reduced or increased. Computer 110 through programmed instructions, electrically signals either electrical solenoid valve 103 or 104 to achieve the desired rubber feed speed change.

As another aspect of operating the type hosiery machine being used by way of example, it is necessary to perform what is called racking the main drum which effectively means indexing the main drum to control the relative positions of certain of the knitting mechanisms including the thread feed fingers according to the portion of the stocking being knit. This racking or indexing operation is coordinated with forming the welt, leg, ankle and toe portions of the stocking with conventional reciprocating and other knitting mechanisms controlled off the main drum. In some instances, conventional practice requires that there be a so-called half rack or half throw of the main drum whereas in other cases it is desirable according to conventional knitting practice to have a full rack or full throw of the main drum for effecting a change in position of the main drum and thereby effect a particular change in the conventional knitting machine control mechanisms. The manner in which the main drum is racked by controlling the lifting and lowering of a pawl is explained in the book "Principles of Knitting" by William E. Shinn, 3rd Edition, 1957, published by Clark Publishing Company of Charlotte, N.C. With this background in mind, FIG. 19 schematically illustrates the manner in which the invention provides for programmed controlled half rack and full rack indexing of the main drum. In FIG. 19, there is shown for reference a portion of the base of the clutch shipper fork 140, the clutch shipper shaft 141, the ratchet pawl lifter plate 142, the horizontal raising rod 143, and a modified somewhat lengthened ratchet pawl lifter 145. A frame support member 146 mounts an air solenoid 147 which, when energized, raises the ratchet pawl lifter 145 sufficient to accomplish a half rack or half throw of the main drum, not shown, through the clutch shipper shaft 141. Frame member 146 also mounts a second air solenoid 148 which when energized is arranged to raise the ratchet pawl lifter 145 in a longer stroke so as to accomplish a full rack or full throw of the main drum through clutch shipper shaft 141. As further illustrated in FIG. 19 the respective air solenoids 147, 148 are controlled through electrically operated solenoid valves 150, 151 connected to a suitable controller 152 which in turn is connected to the computer 110. For those familiar with the conventional racking operation of the type hosiery machine being used by way of example, it can be seen that by establishing control pulses under program control, such pulses fed from computer 110 through controller 152 to the respective electrical solenoid valves 150, 151 enable the main drum to be selectively racked either in a half rack or full rack according to the program requirements associated with the particular stocking being knit. The description next refers to the mechanism and control system associated with controlling the cylinder height as a means of controlling the stitch length and thereby, in conjunction with the rubber feed speed control, controlling the compressive effect of the stocking.

Stitch length and consequently the compressive effect of the stocking fabric may be controlled on the type circular knitting machine being used by way of example by various means including raising and lowering the stitch cams or raising and lowering the cylinder with respect to the cams. In either case the known mechanical mechanisms have been previously used to selectively provide a relatively loose stitch as in FIG. 13 or a relatively tight stitch as in FIG. 14. The apparatus and method of the invention brings to this known practice, the practice of enabling program control to establish the tightness of the stitch for a desired pressure profile and in the present embodiment is based on using cylinder height control as the stitch length control. The invention mechanism and control apparatus for this purpose is schematically illustrated in FIGS. 20-21.

Figure 13:
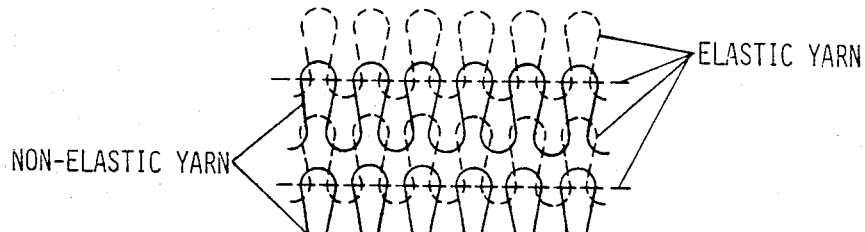
FIG. 13 is a fabric stitch diagram for a relatively low compression fabric.
Figure 14:
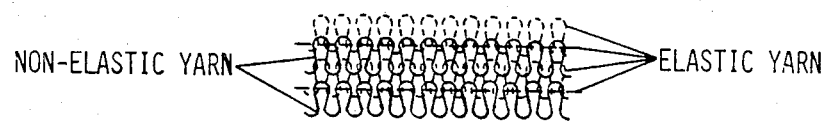
FIG. 14 is a fabric stitch diagram for a relatively high compression fabric.
Figure 21:
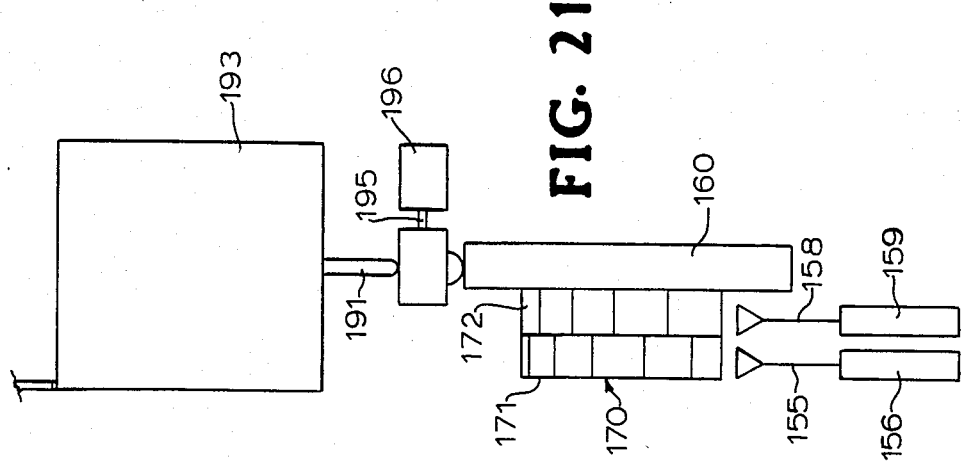
FIG. 21 is a front and somewhat schematic elevation view of the cylinder height control seen in FIG. 20.
Figure 20:
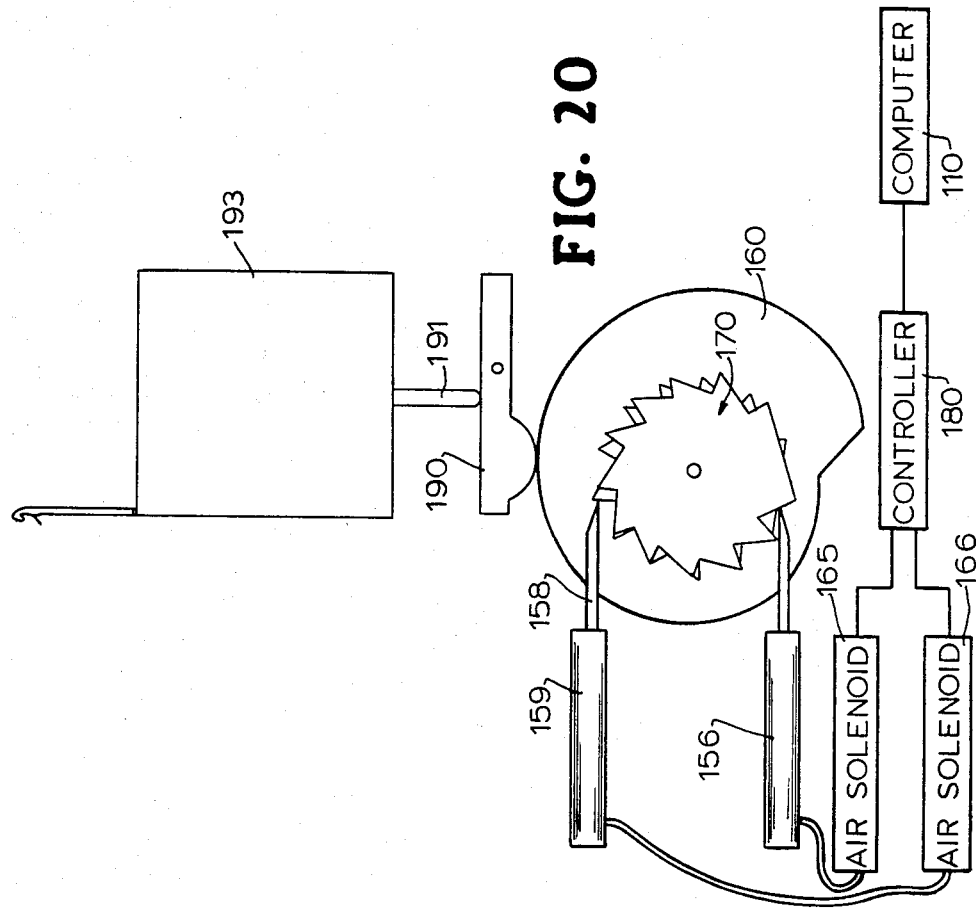
FIG. 20 is a side and somewhat schematic elevation view of the cylinder height control.
Figure 22:
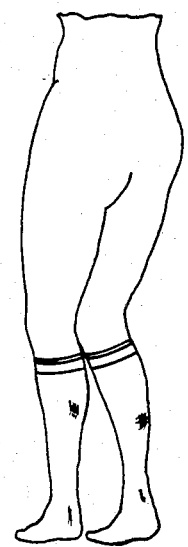
FIGS. 22, 23, 24 and 25 illustrate respectively below-knee-type, above-knee-type, one-leg-leotard-type and leotard-type compressive hosiery products of the type which can be made according to the invention.
Figure 23:
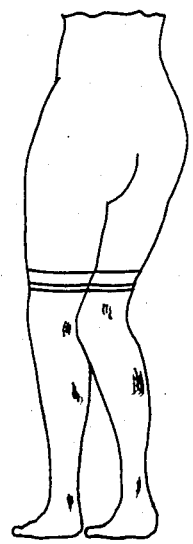

In FIGS. 20-21, there is shown a progressive linear lobe cam 160 secured to a gear set 170 comprising a pair of gears 171, 172, each having respective sets of 12 teeth corresponding to 12 cylinder height positions. As with the linear lobe cam 115 used for controlling the rubber feed speed, use of linear lobe cam 160 facilitates use of program control to obtain uniform mechanical responses to computer commands. Each mechanical change is thus in a predetermined amount and overall leads to a smooth mechanical transistion from change to change. Gear 171 is actuated by a pawl 155 controlled by an air cylinder 156 and gear 172 is actuated by a pawl 158 actuated by air cylinder 159. The air cylinders 156, 159 are controlled through respective electric air solenoid valves 165, 166 connected through a suitable controller 180 to computer 110. Lobe cam 160 is thus positioned in one direction or the other dependent on which of the two air cylinders 156, 159 are energized which is in turn dependent on which of the electrical solenoid control valves 165, 166 is energized through controller 180 by the selection program established by computer 110. Bidirectional positioning of lobe cam 160 controls positioning of follower arm 190 connected through linkage 191 so as to raise and lower cylinder 193. Arm 190 pivots on a shaft 195 mounted on a support 196 suitably fixed to the machine frame. Since cylinder height positioning as such has been previously known (see for example the book "Principles of Knitting" previously referred to) those skilled in the art will readily appreciate from the schematic illustration of FIGS. 20-21 and the brief description given how computer 110 controls the position of cylinder 193 under program control and thereby controls the looseness and tightness of the stitch as depicted in FIGS. 13-14 to obtain a selected pressure profile.

In summary, the invention in a broad sense offers the possibility of being able to customize tubular fabric goods to a specific body contour and desired compression profile for such contour. Looked at broadly, the invention also offers the possibility of forming such tubular goods either from tubular fabric or from flat fabric having known circumferential compression characteristics when fabricated into tubular form. As specifically applied to the art of compressive stockings, and as best seen in the overall method diagrams of FIGS. 10A-10C and FIG. 11 and the overall system diagram of FIG. 12, the invention brings to the art at least the following features not heretofore known:

1. The ability to knit a compressive stocking according to a specific patient's prescription.
2. The ability to obtain an optimized and variable pressure profile in a compressive stocking.
3. The ability to analyze a patient's physical data, the physician's prescription and known pressure circumference-machine setting data and from this calculate through a computer manipulation those machine settings suited to the needs of the patient and using program control knit a compressive stocking suited to such needs.
4. An improved compressive stocking, per se, having significantly improved pressure profile characteristics based on graduated and controlled changes in both limp width and stitch density.
5. An improved measuring device for recording patient information and particularly control point information suited to computer entry as related to a compressive stocking.
6. The method of using a single size circular knitting machine to knit compressive stockings under program control for a wide range of circumference-pressure combinations.
7. The method of using controllable elements on a circular knitting machine over a wide range of combination settings to establish fabric samples having a comparable wide range of pressure-circumference characteristics, measuring, storing and analyzing such characteristics to produce a data bank enabling correspondence between combinations of machine settings and pressure-circumference characteristics in a desired pressure profile.

With what has been said, it can also be seen that the method of the invention lends itself to rapid and precise reproduction of a compressive stocking made from woven fabric with predetermined compression characteristics suited to a particular patient's needs. That is, the described method of testing flat knitted fabric samples for tensile properties and forming tubular fabric goods therefrom, as described in connection with FIGS. 26 and 27, lends itself to forming other tubular fabric goods from flat fabric of predetermined and known tensile characteristics utilizing the teachings of the invention as applied to circular knit compressive stockings. The test fabric data file thus lends itself to being built up from both tubular as well as flat fabric samples knit under a range of machine setting combinations. The invention as illustrated in FIG. 12 also includes the method of establishing and storing standard off-the-shelf stocking information and calling up and comparing such information under program control with the patient's needs to determine whether such off-the-shelf goods meet the patient's needs.

While primarily intended to serve the needs of those patients requiring therapeutic compressive stockings, and the like, it is also recognized that the invention opens up the opportunity for broader application to other types of circular knit goods where circumference and/or pressure are critical characteristics. While a single size circular knitting machine was used by way of example, the invention also contemplates use of knitting machines of varying cylinder size under program control and with each machine assigned to a range of desired circumferences in the finished products produced according to the invention and with either a fine or coarse construction as desired and according to the application.

While conventional practice in the selection and manufacture of compressive stockings dictates the use of a standard pressure profile referenced to the ankle as previously explained, it is also recognized that the method and apparatus of the invention enable essentially any compression profile to be obtained and reproduced when desired. For example, where there is a need for a compressive garment having a substantially uniform pressure profile such as for a patient who has had a portion of a leg amputated, such a garment can now be readily provided. Also, where a patient's particular body contour and medical conditions dictate the need for a special graduated compression profile which does fit the standard profile, such special profile can be readily implemented in the finished garment utilizing the invention. Combinations of graduated and uniform pressure profiles are also readily obtainable and reproducible.

What is claimed is:

1. A method of making a tubular garment fabric forming the entire or some portion of a garment conforming to a selected part of the body such as the leg and in which the fabric is desired to assert some predetermined degree of compression at selected locations along the length thereof and with graduated and controlled changes in such compression between such locations, comprising the steps of:
   (a) knitting on a circular knitting machine having a complement of cooperable knitting elements a series of sample tubular fabrics in which from sample to sample a change is made in the setting of the knitting elements of the machine such that the limp and stretch circumferences and corresponding compression characteristics are changed from sample to sample in correspondence with the machine settings;
   (b) measuring the stretch-compression characteristics of each sample at each of a plurality of stretch positions and storing such measurements together with the corresponding machine settings for each such sample as first memory data;
   (c) measuring the actual circumference at each of some predetermined number of locations along the length of the part of the body on which the tubular garment fabric is to be worn and storing the circumferential measurements thereby obtained together with the compression pressure desired at selected said locations as second memory data;
   (d) operating on said first and second memory data with program means and producing therefrom third memory data representing a set of settings for said machine capable of producing a finished tubular garment fabric suited to the anatomic form of said selected part of the body and exhibiting compression characteristics at each of said selected locations thereon substantially equal to the said desired compression pressures and program determined machine settings corresponding to graduated pressures between said selected locations; and
   (e) operating said machine under program control utilizing said third memory data through control means on said machine adapted to control said selected machine settings under signal control established by said third memory data in timed relation to the operation of said machine whereby to produce a said finished tubular garment fabric having said compression pressures at said selected locations and said graduated pressures therebetween.

2. The method of claim 1 wherein said machine setting change executed from sample to sample comprises a change selected from either or both a rubber feed speed or cylinder height change.

3. The method of claim 2 wherein a change in a said machine rubber feed speed or cylinder height setting is mechanically executed by means of mechanically adjusting under program control the position of a respective linear lobe cam controlling the setting such that the changes are mechanically uniform and effect a smooth mechanical transition.

4. The method of claim 2 including the step of timing the operation of said machine with cylinder revolution counting means adapted to produce an electrical signal for each revolution of the cylinder of said machine and timing the selection of the machine's settings obtained from said third memory data with said revolution counting signals.

5. The method of claim 2 wherein said tubular garment fabric comprises a circular knit tubular fabric having an elastomeric thread and including the step of selecting under program control the dropping and raising of the thread feed associated with said elastomeric thread.

6. The method of claim 5 including the step of timing the operation of said machine with cylinder revolution counting means adapted to produce an electrical signal for each revolution of the cylinder of said machine and timing the selection of the machine settings obtained from said third memory data with said revolution counting signals.

7. The method of claim 6 wherein said machine includes electropneumatic controls for each of said machine settings and including the step of operating said electropneumatic controls by signals determined by said third memory data.

8. The method of claim 1 wherein measuring said sample includes measuring the limp and dead stretch circumferences, a selected number of circumferences therebetween and the compression at each of such circumferences.

9. The method of claim 1 wherein said tubular garment fabric comprises a compressive stocking product.

10. The method of claim 1 wherein said selected part of the body comprises a leg, said finished tubular fabric comprises a compressive stocking product, said selected locations include the ankle and the pressures achieved in the finished compressive product in other measured locations are selected to be a percentage of the pressure achieved at the ankle.

11. The method of claim 1 wherein said tubular garment fabric comprises a circular knit tubular fabric having an elastomeric thread.

12. The method of claim 11 including the step of selecting under program control the dropping and raising of selected thread feeds associated with said machine.

13. A programmable and programmably-controlled apparatus for producing a range of circular knit tubular fabrics each having predetermined desired compressive pressure profile characteristics in selected portions thereof corresponding to a particular application thereof, comprising:
   (a) a circular knitting machine having a needle cylinder and other elements cooperating therewith to form circular knit stretchable tubular fabric including movable knitting elements and machine electrical control means therefor enabling the stretch-compressive characteristic of the tubular fabric to be varied according to the setting of said movable elements by said machine electrical control means; and (b) program storage and control means including:

(i) means for receiving, storing and analyzing measurement data relating non-stretch and stretch circumferences to compression characteristics for a plurality of sample tubular fabrics made on said machine at various machine settings such that within a range of possible circumferences the required machine settings to produce a desired compression for a known measured circumference at a specific location on a selected part of the body, such as the leg, can be determined and including means to make and store such machine setting determinations over said range of possible circumferences as first memory data;

(ii) means for receiving and storing measurement data representing actual measured circumferences at plural selected locations on a selected said part of the body and the desired compression pressures at each such location as second memory data;

(iii) means for operating with said first and second memory data and computing therefrom and storing as third memory data a set of optimized settings for said machine electrical control means to obtain said desired compression pressures in a said tubular fabric; and (iv) means for interfacing said program storage and control means with said machine electrical controls means and for operating said machine electrical control means in correspondence with machine setting control signals responsive to said third memory data and in timed relation with operation of said machine whereby to produce a tubular fabric having said desired compression pressures in a graduated profile.

14. A programmable and programmably-controlled apparatus as claimed in claim 13 wherein said circular knit tubular fabrics comprise elasticized fabrics, said machine includes a source of elastomeric thread fed through a movable feed finger for incorporating said elastomeric thread in said elasticized tubular fabrics and said machine electrical control means includes means for controlling the raising and lowering of said elastomeric thread feed finger.

15. A programmable and programmably-controlled apparatus as claimed in claim 14 wherein said machine electrical control means includes:

(a) auxiliary electrical control means for adjusting the operating height of said needle cylinder to control the length of stitch produced thereon; and (b) auxiliary electrical control means for adjusting the speed of feeding said elastomeric thread to the said needle cylinder.

16. A programmable and programmably-controlled apparatus as claimed in claim 15 including electrical signal means for counting the revolutions of said needle cylinder and producing electrical signals corresponding thereto.

17. A programmable and programmably-controlled apparatus as claimed in claim 15 wherein said auxiliary electrical control means comprise electropneumatic control means.

18. A programmable and programmably-controlled apparatus as claimed in claim 13 including for each of selected said movable knitting elements an operatively associated linear lobe cam mechanism arranged to control the position of the respective movable knitting element with which it is associated and move said respective knitting element in uniform mechanical steps.

19. A method of forming on a circular knitting machine a circular knit fabric garment to be worn by a selected individual, comprising:

(a) measuring the individual to obtain a series of longitudinally-spaced, circumferential dimensions of the portion of the body on which the garment is to be worn, and transferring said measurements to computer memory;

(b) entering in said computer memory:

(i) data representative of the compression desired at selected measuring locations on said body;

(ii) other data representative of the compression obtained in the finished garment when made with selected machine settings and stretched to a known circumference;

(c) operating on all said computer memory data with a program effective to determine and place in said memory a set of machine settings for producing said garment with a compression profile corresponding to said desired pressures at said selected measured locations; and (d) knitting said garment on a circular knitting machine and establishing said settings for said machine under program control utilizing said memory whereby to obtain said garment with said pressure profile.

20. A programmable and programmably-controlled apparatus for producing a desired circular knit tubular fabric having a predetermined desired compression profile in a selected portion thereof, comprising:

(a) a circular knitting machine having a needle cylinder and other elements cooperating therewith to form circular knit stretchable tubular fabric including remotely controllable, movable knitting elements enabling the stretch-compressive characteristic of the tubular fabric to be varied according to the setting of said movable elements; and (b) program control means including:

(i) means to compute from selected physical dimensions of the individual intended to wear a desired tubular fabric having a desired compression profile and from known stretch-compressive characteristics of other tubular fabrics made under known machine settings, the particular set of machine settings required for producing the desired tubular fabric with the desired compression profile and store such computed settings; and (ii) means responsive to said stored computed settings and operative in timed relation with operation of said machine to control said movable elements to produce said desired tubular fabric having said desired compression profile.

21. A method of forming a tubular fabric garment to be worn by a selected individual and having a desired compression profile, comprising:

(a) measuring the individual to obtain a series of longitudinally-spaced, circumferential dimensions of the portion of the body on which the garment is to be worn, and transferring said measurements to computer memory;

(b) entering in said computer memory:
  (i) data representative of the compression desired at selected measuring locations on said body;
  (ii) other data representative of the compressions obtained in finished fabric made with a selected machine and selected machine settings and stretched to known circumferences;

(c) operating on all said computer memory data with a program effective to determine and place in said memory a set of machine settings for said selected machine for producing fabric therewith which in tubular form will exhibit a compression profile corresponding to said desired pressures at said selected measuring locations; and (d) establishing said settings for said machine under program control utilizing said memory and forming said fabric on said selected machine and forming said garment with said fabric whereby to obtain said garment with said pressure profile.

22. A program method of selecting a new tubular fabric garment to be worn on a selected part of the body by a selected individual and requiring a desired compression profile, comprising:

(a) determining and storing in memory first information representative of the pressure profile characteristics of a plurality of previously-made, tubular fabric garments corresponding to a range of body contours for the portion of the body on which the garment is to be worn and a range of pressure profiles for such contours; and (b) determining and storing other second information in memory representative of the contour of said individuals selected part of the body and desired compression profile; and (c) comparing said first and second information to select the previously-made garment closest in pressure profile to said new garment pressure profile.

* * * * *